United States Patent [19]

Usui et al.

[11] Patent Number: 5,869,460
[45] Date of Patent: Feb. 9, 1999

[54] SULFATED AND PHOSPHATED SACCHARIDE DERIVATIVES, PROCESS FOR THE PREPARATION OF THE SAME AND USE THEREOF

[75] Inventors: Toshinao Usui; Takao Igami; Takuji Kakigami; Hitoshi Hamashima; Takahito Jomori; Akira Tashita; Yoshiro Ishiwatari; Shoji Yokochi; Takahiko Mitani, all of Nagoya; Yasuo Suzuki, Shizuoka; Akira Hasegawa, Gifu, all of Japan

[73] Assignee: Sanwa Kaguku Kenkyusho Co., Ltd., Aichi-ken, Japan

[21] Appl. No.: 739,423

[22] Filed: Oct. 29, 1996

[30] Foreign Application Priority Data

Oct. 31, 1995 [JP] Japan .................................. 7-283425
Oct. 22, 1996 [JP] Japan .................................. 8-279362

[51] Int. Cl.⁶ .......................... A61K 31/70; C07H 15/00
[52] U.S. Cl. .............................. 514/25; 514/53; 536/4.1; 536/18.2; 536/18.5; 536/18.6
[58] Field of Search ........................ 514/25, 53; 536/4.1, 536/18.2, 18.5, 18.6

[56] References Cited

PUBLICATIONS

Takada et al. Biochemical and Biophysical Research Communication, vol. 179, No. 2, Sep. 16, 1991, pp. 713–719, "Adhesion of Human Cancer Cells to Vascular Endothelium Mediated".

Handa et al. Biochemical and Biophysical Research Communication, vol. 181, No. 3, Dec. 31, 1991, pp. 1223–1230, "Selectin GMP–140 (CD62; PADGEM) Binds to Sialosyl–Le$^a$ and Sialosyl–Le$^x$, and Sulfated Glycans Modulate This Binding".

Suzuki et al. Biochemical and Biophysical Research Communication, vol. 190, No. 2, Jan. 29, 1993, pp. 426–434, "Sulfated Glycolipids are Ligands for a Lymphocyte Homing Receptor, L–Selectin (LECAM–1), Binding Epitope in Sulfated Sugar Chain".

DeBruyne et al. Carbohydrate Research 25 (1972), pp. 59–65, "The Acid Hydrolysis of Alkyl β–D–Galactopyranosides".

Furui et al. Carbohydrate Research 229 (1992), pp. C1–C4, "Synthesis of 1–deoxynojirimycin–containing Glycans Related to the Lewis X and Sialyl–Lewis X Epitopes Recognized by LEC–CAMs".

Hasegawa et al. Carbohydrate Research 257 (1994), pp. 67–80, "Synthesis of Deoxy–L–Fucose–Containing Sialyl Lewis X Ganglioside Analogues".

Mulligan et al. The Journal of Immunology, vol. 151, No. 11, Dec. 1, 1993, pp. 6410–6417, "Protective Effects of Selectin Chimeras in Neutrophil–Mediated Lung Injury".

Mulligan et al. The Journal of Immunology, vol. 152, 1994, pp. 832–840, "Requirements for L–Selectin in Neutrophil–Mediated Lung Injury in Rats".

Jutila et al. The Journal of Immunology, vol. 153, pp. 3917–3928 (1994), "Cell Surface P–and E–Selectin Support Shear–Dependent Rolling of Bovine γ/δ T Cells".

Mulligan et al. International Immunology, vol. 7, No. 7, pp. 1107–1113 (July 1995), "Anti–Inflammatory Effects of Sulfatides in Selectin–Dependent Acute Lung Injury".

Mulligan et al. J. Clin. Invest., vol. 88, Oct. 1991, pp. 1396–1406, "Role of Endothelial–Leukocyte Adhesion Module 1 (ELAM–1) in Neutrophil–Mediated Lung Injury in Rats".

Mulligan et al. J. Clin. Invest., vol. 90, Oct. 1992, pp. 1600–1607, "Neutrophil–Dependent Acute Lung Injury".

Mulligan et al. Nature, vol. 364, Jul. 8, 1993, pp. 149–151, "Protective Effects of Oligosaccharides in P–Selectin–Dependent Lung Injury".

Graves et al. Nature, vol. 367, Feb. 10, 1994, pp. 532–538, "Insight Into E–Selectin/Ligand Interaction from the Crystal Structure and Mutagenesis of the lec/EGF Domains".

Polley et al. Proc. Natl. Acad. Sci., Vol. 88 pp. 6224–6228, Jul. 1991, "CD62 and Endothelial Cell–Leukocyte Adhesion Molecule 1 (ELAM–1) Recognize the Same Carbohydrate Ligand, Sialyl–Lewis x".

Bajorath et al. Biochemistry, vol. 33, pp. 1332–1339 (1994), "CD62/P–Selectin Binding Sites for Myeloid Cells and Sulfatides are Overlapping".

(List continued on next page.)

Primary Examiner—Kathleen K. Fonda
Attorney, Agent, or Firm—Nikaido Marmelstein Murray & Oram, LLP

[57] ABSTRACT

There are described sulfated and phosphated saccharide erivatives of the Formula

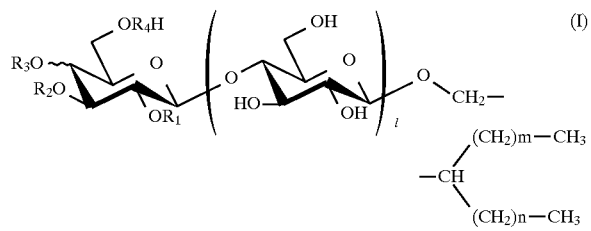

wherein $R_1$ is hydrogen atom or a residue of sulfate, phosphate or L-fucose; $R_2$, $R_3$ and $R_4$ are hydrogen atom or a residue of sulfate or phosphate, respectively; 1 is an integer of 0 or 1;
m is an integer of 0–15; and n is an integer of 0–21, or pharmaceutically acceptable salts thereof, a process for the preparation of the derivatives and salts as well as use thereof, as an anti-inflammatory agent.

6 Claims, No Drawings

OTHER PUBLICATIONS

Hasegawa et al. Biosci. Biotech. Biochem., vol. 59, pp. 1091–1094 (1995), "Synthesis of a Sialyl Lewis X Ganglioside Analogue Containing N–Glycolyl in Place of the N–Acetyl Group in the N–Acetylneuraminic Acid Residue".

Aruffo et al. Cell, vol. 67, pp. 35–44, Oct. 4, 1991, "CD62/P–Selectin Recognition of Myeloid and Tumor Cell Sulfatides".

Rao et al. The Journal of Biological Chemistry, vol. 269, No. 31 (Aug. 5, 1994), "Sialyl Lewis X Mimics Derived from a Pharmacophore Search are Selectin Inhibitors with Anti–Inflammatory Activity".

Mulligan et al. J. Exp. Med., vol. 178, pp. 623–631, Aug. 1993, "Protective Effects of Sialylated Oligosaccharides in Immune Complex–Induced Acute Lung Injury".

Phillips et al. Science, vol. 250, pp. 1130–1132 (Nov. 23, 1990), "ELAM–1 Mediates Cell Adhesion by Recognition of a Carbohydrate Ligand, Sialyl–Le$^x$".

SULFATED AND PHOSPHATED SACCHARIDE DERIVATIVES, PROCESS FOR THE PREPARATION OF THE SAME AND USE THEREOF

BACKGROUND OF THE INVENTION

1. Field of the Invention

The present invention relates to novel sulfated and phosphated saccharide derivatives, process for the preparation of the same and use thereof as well as an anti-inflammatory agent containing the derivative as an effective ingredient thereof.

2. Related Arts

In recent years, many adhesion molecules have been identified which concern direct cell contact between cells per se or cell and exo-cellular matrix. These adhesion molecules are classified into groups of selectin family, immunoglobulin family, integrin family, CD44 and the like in view of those structural characteristics, and elucidation of various functions thereof have energetically been made. Many of cell adhesion molecules belonging to the selectin family concern immunophlogistic reactions.

At the present time, 3 type cell adhesion molecules (L-selectin, E-selectin and P-selectin) have been known as those belonging to the selectin family. Among them, L-selectin is expressed on a lymphocyte, neutrocyte and monocyte, and it has been considered as concerning to homing of the lymphocyte and adhesion of inflamed region to vascular endothelium cells. E-selectin is a protein to be expressed on inflammatory vascular endothelium cells by stimulation of inflammatory cytokine, and mediates the cell adhesion of a neutrocyte, monocyte and the like. While, P-selectin expresses on activated vascular endothelium cells and activated platelets, and mediates cell adhesion between a platelet and leukocyte or the vascular endothelium cell and leukocyte. It become clear that these selectins concern rolling on the surface of vascular endothelium cells of the leukocyte rather than those powerful cell adhesing action thereto, which rolling occurs prior to the cell adhesion ["J. IMMUNOL.", Vol. 153, page 3917 (1994)].

Recently, saccharide ligands recognizing these selectins have been elucidated in molecular level ["NATURE", Vol. 367, page 532 (1994); and "BIOCHEMISTRY", Vol. 33, page 1332 (1994)]. Particularly, it has been found that Sialyl Lewis X and Sialyl Lewis A is a common ligand of E-, L- and P-selectins ["SCIENCE", Vol. 250, page 1130 (1990); "SCIENCE", Vol. 250, page 1132 (1990); "PROC. NATL. ACAD. SCI. USA", Vol. 88, page 6224 (1991); "BIOCHEM, BIOPHY. RES. COM.", Vol. 179, page 713 (1991) and "J. BIOL. CHEM.", Vol. 269, page 19663 (1994)], and various derivatives thereof have been synthesized ["PROC. NATL. ACAD. SCI. USA", Vol. 88, page 10372 (1991); "CARBOHYDR. RES.", Vol. 229, page c1 (1992); "CARBOHYDR. RES.", Vol. 257, page 67 (1994) and "BIOSCI. BIOTECH. BIOCHEM." Vol. 59, page 1091 (1995)]. Further, it has been found that a sulfated saccharide chain as in that of sulfatides and a phosphated poly alcohols strongly bind to selectins and more particularly to P- and L-selectins and thus such a report has been issued that such compounds may show anti-inflammatory action ["CELL", Vol. 67, page 35 (1991); "BIOCHEM. BIOPHY. RES. COM.", Vol. 181, page 1223 (1991); "BIOCHEM. BIOPHY. RES. COM.", Vol. 190, page 426 (1993) and "INT. IMMUNOL.", Vol. 7, page 1107 (1995)].

On the other hand, an acute lung damage model using cobra venom factor (CVF) has been established as selectin depending inflammation model "J. CLIN. INVEST.", Vol. 88, page 1396 (1991); "J. CLIN. INVEST.", Vol. 90, page 1600 (1992) and "J. IMMUNOL.", Vol. 151, page 6410 (1993)].

Recently, such reports have been issued as on screening using anti-selectin antibody ["J. IMMUNOL." Vol. 152, page 832 (1994)], Sialyl Lewis X ["NATURE", Vol. 364, page 149 (1993) and "J. EXP. MED.", Vol. 178, page 623 (1993)]or sulfatide ["INT. IMMUNOL.", Vol. 7, page 1107 (1995)] and the like, and thus it has been recognized that inhibition of cell adhesion due to selectin shows an inflammatory effect in various inflammatory reactions such as ischemia reperfusion disease, asthma, skin inflammation, lung injury due to activated complements, a shock caused by bleeding or external wound and rheumatism.

As sulfatide analogues, P. A. Ward et al. have reported that sulfatide and synthetic sulfated galactose derivatives (containing 2-tetradesyl haxadesyl β-D-galactopyranoside 3-sulfate) shows inflammation inhibition effect, in case of using 2 type lung injury models, namely an inflammatory model caused activation of whole body complements by administration of CVF and another inflammatory model administrated lgG immunocomplex ["INT. IMMUNOL.", Vol. 7, page 1107 (1995)]. Further, Y. Suzuki et al. have confirmed through in vitro test using a plastic plate that natural and chemically synthesized sulfated glycolipids [containing 2-tetradesyl hexadesyl β-D-galactopyranoside 3-sulfate and 2-tetradesyl hexadesyl O-β-D-galactopyranosyl-(1→4)-β-D-glucopyranoside 3'-sulfate] show a binding specificity to L-selectin ["BIOCHEM. BIOPHY. RES. COM.", Vol. 190, page 426 (1993)]. These results give a suggestions that the selectin adhesion inhibitor may be employed as an effective ingredient of a novel curing or preventive drug for its clinical use.

SUMMARY OF THE INVENTION

An object of the present invention is to provide a novel selectin adhesion inhibiting compound which shows excellent inflammatory effect, has excellent safety in use and stability, and can be produced in commercial scale to use the same as an effective ingredient for preventing or curing drug of inflammatory diseases on vascular wall as well as curing drugs on ARDS, septicemia, rheumatism, shock, nephritis and the like.

The inventors have energetically studied and investigated to finally find that certain sulfated or phosphated saccharide derivatives are suitable for attaining the object, so that the invention was established.

According to the invention, the object can be attained by sulfated or phosphated saccharide derivatives shown by a formula of

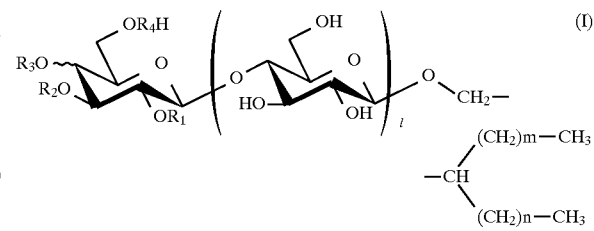

wherein $R_1$ is hydrogen atom or a residue of sulfate, phosphate or L-fucose; $R_2$, $R_3$ and $R_4$ are hydrogen atom or a residue of sulfate or phosphate, respectively; 1 is an integer of 0 or 1;

m is an integer of 0–15; and n is an integer of 0–21.
or a pharmaceutically acceptable salt thereof.

As examples of the β-D-galactose derivatives and β-D-lactose derivatives of compound (I), following compounds can be listed: 2-methylpropyl β-D-galactopyranoside 3-sulfate, 2-methylpropyl β-D-galactopyranoside 6-sulfate, 2-methylpropyl β-D-galactopyranoside 3,6-disulfate, 2-methylpropyl,8-D-galactopyranoside 3,4,6-trisulfate, 2-methylpropyl β-D-galactopyranoside 2,3,4,6-tetrasulfate, 2-propylpentyl β-D-galactopylanoside 3-sulfate, 2-propylpentyl β-D-galactopyranoside 6-sulfate, 2-propylpentyl β-D-galactopyranoside 3,6-disulfate, 2-propylpentyl β-D-galactopyranoside 2,3,6-trisulfate, 2-propylpentyl β-D-galactopyranoside 2, 3, 4, 6-tetrasulfate, 2-hexadesyltetracosyl β-D-galactopyranoside 3-sulfate, 2-methylpropyl O-β-D-galactopyranosyl-(1→4)-β-D-glucopyranoside 3'-sulfate, 2-methylpropyl O-β-D-galactopyranosyl-(1→4)-β-D-glucopyranoside 3',6'-disulfate, 2-propylpentyl β-D-galactopyranosyl-(1→4)-β-D-glucopyranoside 3'-sulfate, 2-propylpentyl O-β-D-galactopyranosyl-(1→4)-β-D-glucopyranoside 3',6'-disulfate, 2-tetradecylhexadecyl O-β-D-galactopyranosyl-(1→4)-β-D-glucopyranoside 3',6'-disulfate, 2-tetradecylhexadecyl O-β-D-galactopyranosyl-(1→4)-β-D-glucopyranoside 3',6',6-trisulfate, 2-methylpropyl β-D-galactopyranoside 2,3,4,6-tetraphosphate, 2-propylpentyl β-D-galactopyranoside 2,3,4,6-tetraphosphate, 2-tetradecylhexadecyl β-D-galactopyranoside 2,3,4,6-tetraphosphate, 2-methylpropyl β-D-galactopyranoside 3,4-diphosphate, 2-propylpentyl β-D-galactopyranoside 3,4-diphosphate, 2-tetradecylhexadecyl β-D-galactopyranoside 3,4-diphosphate, 2-propylpentyl β-D-glucopyranoside 3-triphosphate, 2-propylpentyl β-D-glucopyranoside 2,3-diphosphate, 2-propylpentyl β-D-galactopyranoside 2,3,4-triphosphate, 2-propylpentyl O-β-D-galactopyranosyl-(1→4)-β-D-glucopyranoside 3',4'-diphosphate, 2-tetradecylhexadecyl O-β-D-galacto-pyranosyl-(1→4)-β-D-glucopyranoside 3',4'-diphosphate, 2-propylpentyl O-α-L-fucopyranosyl-(1→2)-β-D-galactopyranoside 3-sulfate, 2-propylpentyl O-α-L-fucopyranosyl-(1→2)-β-D-galactopyranoside 3,3'-disulfate, 2-propylpentyl O-α-L-fucopyranosyl-(1→2)-β-D-galactopyranoside 3,6-disulfate, 2-propylpentyl O-α-L-fucopyranosyl-(1→2)-β-D-galactopyranoside 3,3',6-trisulfate, 2-tetradecylhexadecyl O-α-L-fucopyranosyl-(1→2)-β-D-galactopyranoside 3-sulfate, 2-tetradecylhexadecyl O-α-L-fucopyranosyl-(1→2)-β-D-galactopyranoside 3,3'-disulfate, 2-tetradecylhexadecyl O-α-L-fucopyranosyl-(1→2)-β-D-galactopyranoside 3,3'-disulfate, 2-tetradecylhexadecyl O-α-L-fucopyranosyl-(1→2)-β-D-galactopyranoside 3,3',6-trisulfate, 2-propylpentyl O-α-L-fucopyranosyl-(1→2)-β-D-galactopyranoside 3-phosphate, 2-propylpentyl O-α-L-fucopyranosyl-(1→2)-β-D-galactopyranoside 3,3'-diphosphate, 2-tetradecylhexadecyl O-α-L-fucopyranosyl-(1→2)-β-D-galactopyranoside 3-phosphate, 2-tetradecylhexadecyl O-α-L-fucopyranosyl-(1→2)-β-D-galactopyranoside 3,3'-diphosphate and salts thereof.

According to a process of the invention, the derivatives shown by Formula (I) and salts thereof can be prepared by reacting a compound shown by a Formula

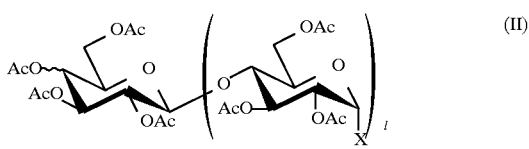

wherein 1 has the meaning as referred to above; and X is a removable group, and a compound shown by a Formula

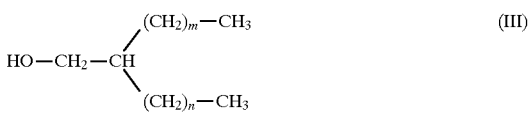

wherein m and n have the meanings as referred to, reacting the resulting saccharide derivative shown by a Formula

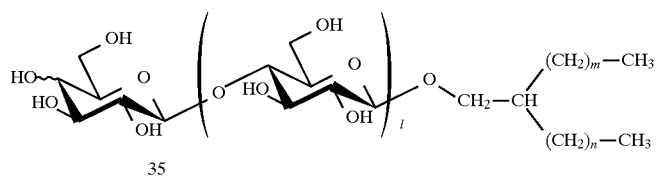

wherein 1, m and n have the meanings as referred to, with a complex of sulfite and trimethyl ammonium or with the complex after having reacted with di-n-butyl-tin oxide to make the saccharide derivative into its tin-acetal derivative, in case of inserting a sulfate group in desired position; or reacting the saccharide derivative, if necessary, with 2,2-dimethoxy propane and then with a benzyl halide to protect a group in desired position in a conventional manner, removing the protection group, and then reacting with dibenzoyloxy (diisopropylamino) phosphine and 1H-tetrazole, in case of inserting a phosphate group in desired position, and if necessary, converting the resulting sulfated or phosphated saccharide derivative into the salt.

The salt of the compound shown by Formula (I) means, of course, pharmaceutically acceptable one, and sodium, potassium and the like alkali metals as well as ammonium and the like can be listed as actions for forming the salt.

The reaction of the compound (II) (a residue of glicosyl-halide with bromine, chlorine, fluorine or the like and glicosylimidate with trichloroacetoimino, N-methylacetoimino or the like radical can be listed as the removable group) with the compound (III) can be carried out by stirring for 0.5–24 hours at −30°–+150° C. in an inert solvent. Such a solvent may be exemplary listed as benzene, toluene, xylene or the like aromatic hydrocarbon; diethylether, tetrahydrofuran, dioxane or the like ether; methylene chloride, chloroform or the like halogenated hydrocarbon; ethyl acetate, acetonitrile, dimethylformamide, dimethylsulfoxide, acetone or the like as well as a mixture of these solvents. For this reaction, quarternary ammonium salt; mercury bromide, silver trifluoromethanesulfonate, mercury perchloric silver or the like heavy metal salt; boron trifluoride ethyl etherate, trimethylsylyltrifullert or the like can be used as an activating agent. Subsequent reaction for removing the protection group is carried out in the presence of a base such as sodium carbonate, potassium carbonate or the like alkaline carbonate; sodium bicarbonate or the like alkaline bicarbonate; sodium hydroxide, potassium hydroxide or the like alkaline hydroxide; triethylamine or the like t-amine.

In case of introducing a residue of sulfate, the resulting saccharide derivative shown by Formula (IV) {however, the compound, wherein 1, m, and n are 0, respectively has been known ["CARBORYD. RES."Vol. 25, page 59 (1972)]} is reacted with di-n-butyl-tin oxide in an inert solvent such as benzene, toluene, xylene or the like aromatic hydrocarbon; diethylether, tetrahydrofuran, dioxane or the like ether; methylene chloride, chloroform or the like halogenated hydrocarbon; methanol, ethanol, or the like alcohol; ethyl acetate, acetonitrile, dimethylformamide, dimethylsulfoxide, acetone or the like and using a moisture removing fractional distillation equipment to make the saccharide derivative into its tin-acetal derivative, and further reacting with suitable amount of a complex of sulfite and trimethyl ammonium.

While, in case of introducing a residue of phosphate, the saccharide derivative shown by Formula (IV) is acetonated by using 2,2-dimethoxy propane to protect remaining hydroxy radicals with a residue of benzyl bromide, if necessary, in an inert solvent such as benzene, toluene, xylene or the like aromatic hydrocarbon; diethylether, tetrahydrofuran, dioxane or the like ether; methylene chloride, chloroform or the like halogenated hydrocarbon; ethyl acetate, acetonitrile, dimethylformamide, dimethylsulfoxide, acetone or the like, hydrolyzing isopropyridene radical with trifluoroacetic acid, and then reacting with the resulting protected compound with dibenzyloxy (diisopropylamino) phosphine and 1H-tetrazole.

When a medicine shall be prepared by using the compound (I) or salt thereof as an effective ingredient, there is no limitation in form of the medicine and thus it can be made into a tablet, pill, capsule, powder, granule, suppository or the like solid preparation; or a solution, suspension, emulsion or the like liquid preparation. For preparing the solid preparation, starch, lactose, glucose, calcium phosphate, magnesium stearate, carboxymethyl cellulose, or the like filler can be used and if necessary, a lubricant, disintegrator, coating agent, coloring matter and the like may also be used. The liquid preparation may contain a stabilizer, dissolution aid, suspending agent, emulsifier, buffer, preservative and the like. In view of stability, the liquid preparation may be charged into a vial or the like and then lyophilized for preservation. The lyophilized powder is dissolved into refined water, when it shall be used, Furthermore, the liquid preparation may contain an isotonic agent, stabilizer, preservative, analgesic additive or the like.

An amount of dose of the compound (I) or salt thereof depends on a kind of the compound, form of the medicine, extent of disease, age of a patient and other factors, but in general, such a range of about 0.1–100 mg/day is preferable for an adult.

DETAILED DESCRIPTION OF PREFERRED EMBODIMENTS

The invention will now be further explained in more detail with reference to Manufacturing Examples, Pharmacological Test Example and Medicine Preparation Examples.

EXAMPLE 1

Sodium 2-methylpropyl β-D-galactopyranoside 3-sulfate (1-1) and disodium 2-methylpropyl β-D-galactopyranoside 3,6-disulfate (1-2)

A mixture of 2-methylpropyl β-D-galactopyranoside (100 mg), di-n-butyl-tin oxide (116 mg) in toluene (10 ml) was refluxed for 16 hours while removing moisture by fractional distillation and the solvent was distilled out in vacuo. To the residue, N,N-di-methylformamide (1 ml) and a complex of sulfurous acid and trimethyl ammonium (70.8 mg) were added to stir for 6 hours at room temperature, methanol (4 ml) was added thereto, and then the solvent was distilled out in vacuo. After separated and refined by silica-gel chromatography (methanol:chloroform=1:1), the residue was treated with cation exchange resin [AG 50W-X8 Resin (Bio-Rad Co.) 1×5 cm], the solvent was distilled out in vacuo, and then lyophilized to afford desired compounds of sodium 2-methylpropyl β-D-galactopyranoside 3-sulfate (52 mg) disodium 2-methylpropyl β-D-galactopyranoside 3,6-disulfate (15 mg).

Compound 1-1
Mass spectrum (FAB$^-$) m/z:
315 (M−Na)$^-$, 337 (M−H)$^-$.
$^1$H-NMR (270 MHz) spectrum (CD$_3$OD) δppm:
0.92 (3H, d, J=6.8 Hz, CH$_3$),
0.93 (3H, d, J=6.88 Hz, CH$_3$),
1.8–2.0 (1H, m, Me$_2$CH),
3.31 (1H, dd, J=7.8, 9.8 Hz, Me$_2$CHCHaHb),
3.53 (1H, dt, J=1.0, 6.3 Hz, H5),
3.66 (1H, dd, J=7.8, 9.8 Hz, Me$_2$CHCHaHb),
3.69 (1H, dd, J=7.8, 8.8 Hz, H2),
3.73 (2H, d, J=6.3 Hz, H6, H6'),
4.21 (1H, dd, J=3.4, 8.8 Hz, H3),
4.24 (1H, dd, J=1.0, 3.4 Hz, H4),
4.29 (1H, d, J=7.8 Hz, H1).
Compound 1-2
Mass spectrum (FAB$^-$) m/z:
417 (M−Na)$^-$, 439 (N−H)$^-$.
$^1$H-NMR (270 MHz) spectrum (CD$_3$OD) δppm:
0.91 (3H, d, J=6.4 Hz, CH$_3$),
0.92 (3H, d, J=6.4 Hz, CH$_3$),
1.8–2.0 (1H, m, Me$_2$CH),
3.31 (1H, dd, J=6.8, 9.3 Hz, Me$_2$CHCHaHb),
3.65 (1H, dd, J=6.8, 9.3 Hz, Me$_2$CHCHaHb),
3.69 (1H, dd, J=7.8, 9.3 Hz, H2),
3.81 (1H, t, J=6.4 Hz, H5),
4.14 (1H, dd, J=6.4, 10.3 Hz, H6'),
4.20 (1H, dd, J=6.4, 10.3 Hz, H6),
4.23 (1H, d, J=9.3 Hz, H3),
4.26 (1H, br, H4),
4.31 (1H, d, J=7.8 Hz, H1).

EXAMPLE 2

Sodium 2-methylpropyl β-D-galactopyranoside 6-sulfate

To 2-methylpropyl β-D-galactopyranoside (100 mg) in N,N-dimethylformamide solution (1 ml), a complex of sulfurous acid and trimethyl ammonium (161 mg) was added to stir for 21 hours at room temperature, and the solvent was distilled out in vacuo. After separated and purified by silica gel chromatography (methanol:chloroform:water=5:8:1), the residue was treated with cation exchange resin [AG 50W-X8 Resin (Bio-Rad Co.) 1×5cm], the solvent was distilled out in vacuo, and then lyophilized to afford the titled compound (76 mg).

Mass spectrum (FAB$^-$) m/z:
315 (M−Na)$^-$, 337 (M−H)$^-$.
$^1$H-NMR (270 MHz) spectrum (CD$_3$OD) δppm:
0.92 (3H, d, J=6.8 Hz, CH$_3$),
0.93 (3H, d, J=6.8 Hz, CH$_3$),
1.8–2.0 (1H, m, Me$_2$CH),
3.28 (1H, dd, J=6.8, 9.8 Hz, Me$_2$CHCHaHb),
3.46 (1H, dd, J=2.9, 9.8 Hz, H3),
3.51 (1H, dd, J=6.3, 9.8 Hz, H2),
3.65 (1H, dd, J=2.9, 9.8 Hz, Me$_2$CHCHaHb),
3.75 (1H, dt, J=1.0, 6.4 Hz, H5),
3.87 (1H, dd, J=1.0, 2.9 Hz, H4),
4.11 (1H, dd, J=6.4, 10.3 Hz, H6'),
4.18 (1H, dd, J=6.4, 10.3 Hz, H6),
4.20 (1H, d, J=6.3 Hz, H1).

EXAMPLE 3

Trisodium 2-methylpropyl β-D-galactopyranoside3,4,6-trisulfate (3-1) and tetrasodium 2-methylpropyl β-D-galactopyranoside 2,3,4,6-tetrasulfate (3-2)

By treating as described in Example 2 excepting that 2-methyl propyl β-D-galactopyranoside (100 mg) and a complex of sulfurous acid and trimethyl ammonium (500 mg) were selected, the titled compound of trisodium 2-methylpropyl β-D-galactopyranoside 3,4,6-trisulfate (24 mg) and tetrasodium 2-methylpropyl β-D-galactopyranoside 2,3,4,6-tetrasulfate (33 mg) were obtained.

Compound 3-1
Mass spectrum (FAB$^-$) m/z:
519 (M−Na)$^-$, 541 (M−H)$^-$.
$^1$H-NMR (270 MHz) spectrum (CD$_3$OD) δppm:
0.92 (3H, d, J=6.8 Hz, CH$_3$),
0.93 (3H, d, J=6.88 Hz, CH$_3$),
1.8–2.0 (1H, m, Me$_2$CH),
3.32 (1H, dd, J=6.8, 9.8 Hz, Me$_2$CHCHaHb),
3.65 (1H, dd, J=7.8, 9.8 Hz, H2),
3.66 (1H, dd, J=7.3, 9.8 Hz, Me$_2$CHCHaHb),
3.95 (1H, dd, J=3.9, 7.8 Hz, H5),
4.20 (1H, dd, J=7.8, 11.7 Hz, H6'),
4.32 (1H, dd, J=3.4, 9.8 Hz, H3),
4.34 (1H, d, J=7.8 Hz, H1),
4.40 (1H, dd, J=3.9, 11.7 Hz, H6),
4.99 (1H, d, J=3.4 Hz, H4).
Compound 3-2
Mass spectrum (FAB$^-$) m/z:
621 (M−Na)$^-$.
$^1$H-NMR (270 MHz) spectrum (CD$_3$OD) δppm:
0.92 (3H, d, J=6.8 Hz, CH$_3$),
0.94 (3H, d, J=6.8 Hz, CH$_3$),
1.8–2.0 (1H, m, Me$_2$CH),
3.32 (1H, dd, J=6.9, 9.3 Hz, Me$_2$CHCHaHb),
3.67 (1H, dd, J=6.4, 9.3 Hz, MezCHCHaHb),
4.01 (1H, dd, J=3.9, 7.3 Hz, H5),
4.21 (1H, dd, J=7.3, 11.7 Hz, H6'),
4.38 (1H, dd, J=3.9, 11.7 Hz, H6),
4.44 (1H, d, J=8.3 Hz, H3),
4.49 (1H, d, J=3.9 Hz, H1),
4.51 (1H, dd, J=3.9, 8.3 Hz, H2),
5.09 (1H, br, H4).

EXAMPLE 4

Sodium 2-pronylpentyl β-D-galactopyranoside 3-sulfate

By treating as described in Example 1 excepting that 2-propylpentyl β-D-galactopyranoside (92 mg) and a complex of sulfurous acid and trimethyl ammonium (52.6 mg) were selected, the titled compound (71 mg) was obtained.

Mass spectrum (FAB$^-$) m/z:
371 (M−Na)$^-$, 393 (N−H)$^1$.
$^1$H-NMR (270 MHz) spectrum (CD3OD) δppm:
0.89 (6H, t, J=6.8 Hz, CH$_3$),
1.2–1.4 (8H, m, CH$_2$CH$_2$),
1.6–1.7 (1H, m, Pr$_2$CH),
3.41 (1H, dd, J=5.9, 9.3 Hz, Pr$_2$CHCHaHb),
3.52 (1H, dt, J=1.0, 6.3 Hz, H5),
3.69 (1H, dd, J=7.8, 9.3 Hz, H2),
3.73 (2H, d, J=6.3 Hz, H6, H6'),
3.81 (1H, dd, J=6.4, 9.3 Hz, Pr$_2$CHCHaHb),
4.21 (1H, dd, J=3.4, 9.3 Hz, H3),
4.24 (1H, dd, J=1.0, 3.4 Hz, H4),
4.27 (1H, d, J=7.8 Hz, H1).
$^{13}$C-NMR (68 MHz) spectrum (CD$_3$OD) δppm:
14.8 (CH$_3$),
20.9 (CH$_2$CH$_2$CH$_3$),
34.7 (CH$_2$CH$_2$ CH$_3$),
39.2 (Pr$_2$CH),
62.3 (C6),
68.5 (C4),
70.2 (C2),
73.9 (Pr$_2$CHCH$_2$),
76.2 (C5),
82.4 (C3),
105.1 (C1).

EXAMPLE 5

Sodium 2-propylpentyl β-D-galactopyranoside 6-sulfate

By treating as described in Example 2 excepting that 2-propylpentyl β-D-galactopyranoside (100 mg) and a complex of sulfurous acid and trimethyl ammonium (56 mg) were selected, the titled compound (59 mg) was obtained.

Mass spectrum (FAB$^-$) m/z:
371 (M−Na)$^-$, 393 (M−H)$^-$.
$^1$-NMR (270 MHz) spectrum (CD$_3$OD) δppm:
0.89 (6H, t, J=6.8 Hz, CH$_3$),
1.2–1.4 (8H, m, CH$_2$CH$_2$),
1.6–1.7 (1H, m, Pr$_2$CH),
3.38 (1H, dd, J=5.9, 9.8 Hz, Pr$_2$CHCHaRb),
3.45 (1H, dd, J=2.0, 9.8 Hz, H3), 3.50 (1H, dd, J=7.3, 9.8 Hz, H2),
3.75 (1H, t, J=6.4 Hz, H5),
3.78 (1H, dd, J=6.3, 9.8 Hz, Pr$_2$CHCHaHb),
3.87 (1H, d, J=2.0 Hz, H4),
4.10 (1H, dd, J=6.4, 10.3 Hz, H6'),
4.18 (1H, dd, J=6.4, 10.3 Hz, H6),
4.18 (1H, d, J=7.3 Hz, H1).
$^{13}$C-NMR (68 MHz) spectrum (CD$_3$OD) δppm:
14.8 (CH$_3$),
20.9 (CH$_2$CH$_2$CH$_3$),
34.6 (CH$_2$CH$_2$CH$_3$),
39.2 (Pr$_2$CH),
67.4 (C6),
69.9 (C4),
72.5 (C2),
73.8 (Pr$_2$CHCH$_2$),
74.1 (C5),
74.8 (C3),
105.3 (C1).

EXAMPLE 6

Disodium 2-propylpentyl β-D-galactopyranoside 3,6-disulfate

By treating as described in Example 2 excepting that 2-propylpentyl β-D-galactopyranoside (104 mg) and a complex of sulfurous acid and trimethyl ammonium (161 mg) were selected, the titled compound (70 mg) was obtained.
Mass spectrum (FAB$^-$) m/z:
473 (M–Na)$^-$, 495 (M–H)$^-$.
$^1$H-NMR (270 MHz) spectrum (CD$_3$OD) δppm:
0.89 (6H, t, J=6.8 Hz, CH$_3$),
1.2–1.4 (8H, m, CH$_2$CH$_2$),
1.6–1.7 (1H, m, Pr$_2$CH),
3.41 (1H, dd, J=5.4, 9.3 Hz, Pr$_2$CHCHaHb),
3.68 (1H, dd, J=7.8, 8.8 Hz, H2),
3.78 (1H, t, J=6.4 Hz, H5),
3.79 (1H, dd, J=5.9, 9.3 Hz, Pr$_2$CHCHaHb),
4.13 (1H, dd, J=6.4, 10.3 Hz, H6'),
4.21 (1H, dd, J=6.4, 10.3 Hz, H6),
4.21 (1H, dd, J=1.0, 8.8 Hz, H3),
4.26 (1H, d, J=1.0 Hz, H4),
4.29 (1H, d, J=7.8 Hz, H1).
$^{13}$C-NMR (68 MHz) spectrum (CD$_3$OD) δppm:
14.8 (CH$_3$),
21.0 (CH$_2$CH$_2$CH$_3$),
34.7 (CH$_2$CH$_2$CH$_3$),
39.2 (Pr$_2$CH),
67.6 (C6),
68.5 (C4),
70.7 (C2),
73.9 (Pr$_2$CHCH$_2$),
73.9 (C5),
81.8 (C3),
105.0 (C1).

EXAMPLE 7

Trisodium 2-propylpentyl β-D-galactopyranoside 2,3,6-trisulfate (7-1) and tetra 2-propylpentyl β-D-galactopyranoside 2,3,4,6-tetra-sulfate (7-2)

By treating as described in Example 2 excepting that 2-propylpentyl β-D-galactopyranoside (102 mg) and a complex of sulfurous acid and trimethyl ammonium (251 mg) were selected, the titled compound of trisodium 2-propylpentyl β-D-galactopyranoside 2,3,6-trisulfate (50 mg) and tetrasodium 2-propylpentyl β-D-galactopyranoside 2,3,4,6-tetrasulfate (128 mg) were obtained.
Compound 7-1
Mass spectrum (FAB$^-$) m/z:
575 (M–Na)$^-$, 597 (M–H)$^-$.
$^1$H-NMR (270 MHz) spectrum (CD$_3$OD) δppm:
0.89 (6H, t, J=6.8 Hz, CH$_3$),
1.2–1.5 (8H, m, CH$_2$CH$_2$),
1.6–1.7 (1H, m, Pr$_2$CH),
3.44 (1H, dd, J=5.9, 9.8 Hz, Pr$_2$CHCHaHb),
3.77 (1H, dd, J=5.9, 9.8 Hz, Pr$_2$CHCHaHb),
3.82 (1H, t, J=6.4 Hz, H5),
4.14 (1H, dd, J=6.4, 10.7 Hz, H6'),
4.21 (1H, dd, J=6.4, 10.7 Hz, H6),
4.37 (1H, d, J=8.3 Hz, H3),
4.38 (1H, br, H4),
4.43 (1H, d, J=7.13 Hz, H1),
4.47 (1H, dd, J=7.3, 8.3 Hz, H2).
$^{13}$C-NMR (68 MHz) spectrum (CD$_3$OD) δppm:
14.8 (CH$_3$),
20.9 (CH$_2$CH$_2$CH$_3$),
34.4 (CH$_2$CH$_2$CH$_3$),
39.0 (Pr$_2$CH),
67.4 (C6),
68.5 (C4),
73.7 (C5),
73.9 (Pr$_2$CHCH$_2$),
77.1 (C2),
80.0 (C3),
103.4 (C$_1$).
Compound 7-2
Mass spectrum (FAB$^-$) m/z:
677 (M–Na)$^-$.
$^1$H-NMR (270 MHz) spectrum (CD$_3$OD) δppm:
0.89 (6H, t, J=6.4 Hz, CH$_3$),
1.2–1.5 (8H, m, CH$_2$CH$_2$),
1.6–1.7 (1H, m, Pr$_2$CH),
3.43 (1H, dd, J=6.4, 9.3 Hz, Pr$_2$CHCHaHb),
3.79 (1H, dd, J=5.9, 9.3 Hz, Pr$_2$CHCHaHb),
4.00 (1H, dd, J=4.4, 7.3 Hz, H5),
4.20 (1H, dd, J=7.3, 11.2 Hz, H6'),
4.38 (1H, dd, J=4.4, 11.2 Hz, H6),
4.4–4.5 (1H, m, H2),
4.4–4.5 (1H, m, H3),
4.47 (1H, br, H1),
5.10 (1H, br, H4).
$^{13}$C-NMR (68 MHz) spectrum (CD$_3$OD) δppm:
14.8 (CH$_3$),
20.9 (CH$_2$CH$_2$CH$_3$),
34.4 (CH$_2$CH$_2$CH$_3$),
39.0 (Pr$_2$CH),
68.4 (C6),
73.5 (C5),
73.8 (Pr$_2$CHCH$_2$),
76.1 (C4), 76.6 (C2),
77.6 (C3),
103.0 (C1).

EXAMPLE 8

Sodium 2-hexadecyltetracosyl β-D-galactopyranoside 3-sulfate

By treating as described in Example 1 excepting that 2-hexadecyltetracosyl β-D-galactopyranoside (100 mg) and a complex of sulfurous acid and trimethyl ammonium (22.5 mg) were selected, the titled compound (65 mg) was obtained.

Mass spectrum (FAB$^-$) m/z:
820.3 (M–Na)$^-$, 842.3 (M–H)$^-$.
H$^1$-NMR (270 MHz) spectrum (CD$_3$OD) δppm:
0.88 (6H, t, J=6.8 Hz, CH$_3$),
1.27 (72H, s, CH$_2$),
1.5–1.7 (1H, m, (C$_{16}$H$_{32}$)(C$_{22}$H$_{45}$)CH),
3.42 (1H, dd, J=5.9, 8.9 Hz, (C$_{16}$H$_{32}$)(C$_{22}$H$_{45}$)CHCHaHb),
3.63 (1H, t, J=5.6 Hz, H5),
3.75 (1H, dd, J=7.9, 12.3 Hz, H2),
3.7–3.9 (2H, m, H6,H6'),
3.76 (1H, dd, J=5.9, 8.9 Hz, (C$_{16}$H$_{32}$)(C$_{22}$H$_{45}$)CHCHaHb),
4.34 (1H, d, J=7.9 Hz, H1),
4.42 (1H, dd, J=3.7, 12.3 Hz, H3),
4.47 (1H, d, J=3.7 Hz, H4).
$^{13}$C-NMR (68 MHz) spectrum (CD$_3$OD—H$_2$O) δppm:
13.9 (CH$_3$),
22.7, 26.8, 26.9, 29.4, 29.7,
29.8, 29.9, 30.3, 31.2, 32.0 (CH$_2$),
38.5 (CH),
61.1 (C6),
67.1 (C4),
69.5 (C2),
73.6 (C5),
73.6 (OCH$_2$),
81.2 (C3),
103.7 (C1).

EXAMPLE 9

Sodium 2-methylpropyl O-β-D-Ralactopyranosyl-(1→4)-β-D-glucopyranoside 3'-sulfate (9-1) and disodium 2-methylpropyl O-β-D-galactopyranosyl-(1→4)-β-D-glucopyranoside 3',6'-disulfate (9-2)

By treating as described in Example 1 excepting that 2-methylpropyl O-β-D-galactopyranosyl-(1→4)-β-D-glucopyranoside (100 mg) and a complex of sulfurous acid and trimethyl ammonium (41.7 mg) were selected, the titled compound of sodium 2-methylpropyl O-β-D-galactopyranosyl-(1→4)-β-D-glucopyranoside 3'-sulfate (96 mg) and disodium 2-methylpropyl O-β-D-galactopyranosyl-(1→4)-β-D-glucopyranoside3',6'-disulfate (8 mg) were obtained.

Compound 9-1
Mass spectrum (FAB$^-$) m/z:
477 (M–Na)$^-$, 499 (M–H)$^-$.
$^1$H-NMR (270 MHz) spectrum (DMSO-d$_6$) δppm:
glucose H1 (4.28, 1H, d, J=7.8 Hz),
H2 (3.2–3.3, 1H, m),
H3 (3.5–3.6, 1H, m),
H4 (3.6–3.7, 1H, m),
H5 (3.3–3.4, 1H, m),
H6, H6' (3.8–3.9, 2H, m),
galactose H1 (4.48, 1H, d, J=7.4 Hz),
H 2 (3.6–3.7, 1H, m),
H3 (4.2–4.3, 1H, m),
H4 (4.2–4.3, 1H, m),
H5 (3.5–3.6, 1H, m),
H6, H6' (3.7–3.8, 2H, m),
aglycon CH$_3$ (0.93, 6H, t, J=6.9 Hz),
CH (1.9–2.0, 1H, m),
OCHaHb (3.3–3.4, 1H, m),
OCHaHb (3.6–3.7, 1H, m).
$^{13}$C-NMR (68 MHz) spectrum (DMSO-d$_6$) δppm:
glucose C1 (104.5),
C2 (74.8),
C3 (76.4),
C4 (81.2),
C5 (76.4),
C6 (62.0).
galactose C1 (105.0),
C2 (70.9),
C3 (81.8),
C4 (68.6),
C5 (76.8),
C6 (62.4),
aglycon CH$_3$ (19.6),
CH (29.7),
OCH$_2$ (77.6).
Compound 9-2
Mass spectrum (FAB$^-$) m/z:
579 (M–Na)$^-$.
$^1$H-NMR (270 MHz) spectrum (DMSO-d$_6$) δppm:
glucose H1 (4.29, 1H, d, J=7.9 Hz),
H2 (3.2–3.3, 1H, m),
H3 (3.5–3.6, 1H, m),
H4 (3.6–3.7, 1H, m),
H5 (3.3–3.4, 1H, m),
H6, H6' (3.8–3.9, 2H, m),
galactose H1 (4.50, 1H, d, J=7.6 Hz),
H2 (3.6–3.7, 1H, m),
H3 (4.2–4.3, 1H, m),
H4 (4.2–4.3, 1H, m),
H5 (3.7–3.8, 1H, m),
H6, H6' (4.0–4.2, 2H, m),
aglycon CH$_3$ (0.93, 6H, t, J=6.9 Hz),
CH (1.9–2.0, 1H, m),
OCHaHb (3.3–3.4, 1H, m),
OCHaHb (3.6–3.7, 1H, m).
$^{13}$C-NMR (68 MHz) spectrum (DMSO-d$_6$) δppm:
glucose C1 (104.7),
C2 (75.0),
C3 (76.5),
C4 (81.1), C5 (76.4),
C6 (62.2),
galactose C1 (104.9),
C2 (70.8),
C3 (81.8),
C4 (68.6),
C5 (74.8),
C6 (66.4),
aglycon $CH_3$ (19.6),
CH (29.7),
$OCH_2$ (77.7).

EXAMPLE 10

Sodium 2-propylpentyl O-β-D-galactopyranosyl-(1→4)-β-D-glucopyranoside 3'-sulfate (10-1) and disodium 2-propylpentyl O-β-D-galactopyranosyl-(1→4)-β-D-glucopyranoside3',6'-disulfate (10-2)

By treating as described in Example 1 excepting that 2-propylpentyl O-β-D-galactopyranosyl-(1→4)-β-D-glucopyranoside (105 mg) and a complex of sulfurous acid and trimethyl ammonium (38.4 mg) were selected, the titled compound of sodium 2-propylpentyl O-β-D-galactopyranosyl-(1→4)-β-D-glucopyranoside 3'-sulfate (95 mg) and disodium 2-propylpentyl O-β-D-galactopyranosyl-(1→4)-β-D-glucopyranoside 3',6'-disulfate (7 mg) were obtained.

Compound 10-1
Mass spectrum ($FAB^-$) m/z:
533 $(M-Na)^-$, 555 $(M-H)^-$.
$^1$H-NMR (270 MHz) spectrum (DMSO-$d_6$) δppm:
glucose H1 (4.23, 1H, d, J=7.9 Hz),
H2 (3.17, 1H, t, J=7.9 Hz),
H3 (3.4–3.5, 1H, m),
H4 (3.4–3.5, 1H, m),
H5 (3.3–3.4, 1H, m),
H6' (3.79, 1H, dd, J=3.0, 12.4 Hz),
H6 (3.86, 1H, dd, J=3.0, 12.4 Hz),
galactose H1 (4.34, 1H, d, J=7.4 Hz),
H2 (3.6–3.7, 1H, m),
H3 (4.18, 1H, dd, J=3.5, 9.9 Hz),
H4 (4.14, 1H, d, J=3.5 Hz),
H5 (3.5–3.6, 1H, m),
H6, H6' (3.6–3.7, 2H, m),
25 aglycon $CH_3$ (0.89, 6H, t, J=6.9 Hz),
$CH_2$ (1.2–1.4, 8H, m),
CH (1.5–1.7, 1H, m),
OCHaHb (3.37, 1H, dd, J=5.9, 9.9 Hz),
OCHaHb (3.75, 1H, dd, J=5.9, 9.9 Hz).
$^{13}$C-NMR (68 MHz) spectrum (DMSO-$d_6$) δppm:
glucose C1 (105.6),
C2 (75.8),
C3 (77.5),
C4 (82.8),
C5 (77.4),
C6 (63.1),
galactose C1 (106.1),
C2 (71.8),
C3 (82.2),
C4 (69.3),
C5 (77.8),
C6 (63.1),
aglycon $CH_3$ (5.6),
$CH_2$ (11.4, 25.1),
CH (29.5),
$OCH_2$ (74.8).

Compound 10-2
Mass spectrum ($FAB^-$) m/z:
635 $(M-Na)^-$.
$^1$H-NMR (270 MHz) spectrum (DMSO-$d_6$) δppm:
glucose H1 (4.24, 1H, d, J=7.9 Hz),
H2 (3.15, 1H, t, J=7.9 Hz),
H3 (3.4–3.5, 1H, m),
H4 (3.4–3.5, 1H, m),
H5 (3.3–3.4, 1H, m),
H6' (3.76, 1H, dd, J=3.0, 12.4 Hz),
H6 (3.89, 1H, dd, J=3.0, 12.4 Hz),
galactose H1 (4.35, 1H, d, J=7.5 Hz),
H2 (3.6–3.7, 1H, m),
H3 (4.20, 1H, dd, J=3.7, 9.9 Hz),
H4 (4.19, 1H, d, J=3.7 Hz),
H5 (3.7–3.8, 1H, m),
H6, H6' (3.9–4.1, 2H, n),
aglycon $CH_3$ (0.89, 6H, t, J=6.9 Hz),
$CH_2$ (1.2–1.4, 8H, m),
CH (1.5–1.7, 1H, m),
OCHaHb (3.40, 1H, dd, J=5.9, 9.9 Hz),
OCHaHb (3.76, 1H, dd, J=5.9, 9.9 Hz).
$^{13}$C-NMR (68 MHz) spectrum (DMSO-$d_6$) δppm:
glucose C1 (105.5),
C2 (75.9),
C3 (77.5),
C4 (82.8),
C5 (77.5),
C6 (63.2),
galactose C1 (106.1),
C2 (71.5),
C3 (82.3),
C4 (69.1),
C5 (75.8),
C6 (67.5),
aglycon $CH_3$ (5.6),
$CH_2$ (11.4, 25.1),
CH (29.6),
$OCH_2$ (74.8).

EXAMPLE 11

Disodium 2-tetradecylhexadecyl O-β-D-galactopyranosyl-(1→4)-β-D-glucopyranoside 3',6'-disulfate (11-1), trisodium 2-tetradecylhexadecyl O-β-D-galactopyranosyl-(1→4)-β-D-glucopyranoside 3',6',6-trisulfate (11-2) and sodium 2-tetradecylhexadecyl O-β-D-galactopyranosyl-(1→4)-β-D-glucopyranoside 3'-sulfate (Na) (11-3)

By treating as described in Example 1 excepting that 2-tetradecylhexadecyl O-β-D-galactopyranosyl-(1→4)-β-D-glucopyranoside (115 mg) and a complex of sulfurous acid and trimethyl ammonium (46.2 mg) were selected, the titled compound of disodium 2-tetradecylhexadecyl O-β-D-galactopyranosyl-(1→4)-β-D-glucopyranoside 3',6'-disulfate (70 mg), trisodium 2-tetradecylhexadecyl O-β-D-galactopyranosyl-(1→4)-β-D-glucopyranoside 3',6',6-trisulfate (30 mg) and sodium 2-tetradecylhexadecyl O-β-D-galactopyranosyl-(1→4)-β-D-glucopyranoside3'-trisulfate (31 mg) were obtained.

Compound 11-1
Mass spectrum (FAB$^-$) m/z:
943.5 (M–Na)$^-$.
$^1$H-NMR (270 MHz) spectrum (DMSO-d$_6$) δppm:
glucose H1 (4.15, 1H, d, J=7.9 Hz),
H2 (3.04, 1H, t, J=7.9 Hz),
H3 (3.3–3.4, 1H, m),
H4 (3.3–3.4, 1H, m),
H5 (3.2–3.3, 1H, m),
H 6 (3.6–3.7, 1H, m),
H6' (3.7–3.8, 2H, m),
galactose H1 (4.36, 1H, d, J=7.9 Hz),
H2 (3.54, 1H, dd, J=9.9 Hz),
H3 (4.0–4.1, 1H, m),
H4 (3.94, 1H, d, J=2.99 Hz),
H5 (3.7–3.8, 1H, m),
H6, H6' (3.8–3.9, 2H, m),
aglycon CH$_3$ (0.86, 6H, t, J=6.9 Hz),
CH$_2$ (1.1–1.4, 52H, m),
CH (1.4–1.6, 1H, m),
OCHaHb (3.2–3.3, 1H, m),
OCHaHb (3.6–3.7, 1H, m).
$^{13}$C-NMR (68 MHz) spectrum (DMSO-d$_6$) δppm:
glucose C1 (103.1),
C2 (73.5),
C3 (75.2),
C4 (80.5),
C5 (75.1),
C6 (60.9).
galactose C1 (103.9),
C2 (68.9),
C3 (79.1),
C4 (66.8),
C5 (73.3),
C6 (65.0),
aglycon CH$_3$ (13.9),
CH$_2$ (22.2, 26.2, 28.8, 29.1, 29.5, 30.5, 31.4)
CH (37.7),
OCH$_2$ (72.2).
Compound 11-2
Mass spectrum (FAB$^-$) m/z:
1045.4 (M–Na)$^-$.
$^1$H-NMR (270 MHz) spectrum (DMSO-d$_6$) δppm:
glucose H1 (4.18, 1H, d, J=7.8 Hz),
H2 (3.07, 1H, t, J=7.8 Hz),
H3 (3.3–3.4, 1H, m),
H4 (3.3–3.4, 1H, m),
H5 (3.4–3.5, 1H, m),
H6 (3.9–4.0, 1H, m),
H6' (4.0–4.1, 2H, m),
galactose H1 (4.43, 1H, d, J=8.3),
H2 (3.4–3.5, 1H, m),
H3 (4.0–4.1, 1H, m),
H4 (3.9–4.0, 1H, m),
H5 (3.7–3.8, 1H, m),
H6, H6' (3.8–4.0, 2H, m),
aglycon CH$_3$ (0.86, 6H, t, J=6.6 Hz),
CH$_2$ (1.1–1.4, 52H, m),
CH (1.4–1.6, 1H, m),
OCHaHb (3.2–3.3, 1H, m),
OCHaHb (3.6–3.7, 1H, m).
$^{13}$C-NMR (68 MHz) spectrum (DRSO-d$_6$) δppm:
glucose C1 (103.0),
C2 (73.1),
C3 (74.9),
C4 (80.3),
C5 (73.1),
C6 (65.2),
galactose C1 (103.5),
C2 (69.1),
C3 (78.6),
C4 (66.7),
C5 (73.3),
C6 (65.0),
aglycon CH$_2$ (13.9),
CH$_2$ (22.2, 26.2, 28,8, 29.2, 29.5, 30.6, 31.4)
CH (37.8),
OCH$_2$ (72.4).
Compound 11-3
Mass spectrum (FAB$^-$) m/z:
841.5 (N–Na)$^-$, 863.5 (M–H)$^-$.
$^1$H-NMR (270 MHz) spectrum (DMSO-d$_6$) δppm:
glucose H1 (4.13, 1H, d, J=7.4 Hz),
H2 (3.00, 1H, t, J=7.4 Hz),
H3 (3.1–3.4, 1H, m),
H4 (3.2–3.4, 1H, m),
H5 (3.1–3.4, 1H, m),
H6, H6' (3.5–3.8, 2H, m),
galactose H1 (4.33, 1H, d, J=7.4 Hz),
H2 (3.4–3.6, 1H, m),
H3 (4.01, 1H, dd, J=3.5, 9.9 Hz),
H4 (3.89, 1H, d, J=3.5 Hz),
H5 (3.4–3.6, 1H, m),
H6, H6' (3.3–3.7, 2H, m),
aglycon CH$_3$ (0.85, 6H, t, J=6.9 Hz),
CH$_2$ (1.30, 52H, s),
CH (1.5–1.7, 1H, m),
OCHaHb (3.2–3.3, 1H, m),
OCHaHb (3.6–3.7, 1H, m).
$^{13}$C-NMR (68 MHz) spectrum (DMSO-d$_6$) δppm:
glucose C1 (102.9),
C2 (73.1),
C3 (74.9),
C4 (81.1),
C5 (74.7),
C6 (60.5),
galactose C1 (103.7), C2 (69.3),
C3 (78.7),
C4 (66.5),
C5 (75.3),
C6 (60.0),
aglycon $CH_3$ (13.8),
$CH_2$ (22.0, 25.9, 28,6, 28.9, 29.3, 30.3, 31.2)
CH (37.5),
$OCH_2$ (72.0).

EXAMPLE 12

Octasodium 2-methylpropyl β-D-galactopyranoside 2,3,4,6-tetranhosphate

To a suspension of 2-methylpropyl β-D-galactopyranoside (100 mg) and 1H-tetrazole (356 mg) in a mixture of dichloromethane and acetonitrile (1:1, 5 ml), dibenzyloxy (diisopropylamino) phosphine (1.17 g) was added to stir for 2 hours at room temperature under argon atmosphere. Then, water (10 ml), ruthenium chloride (2 mg) and sodium periodate (724 mg) were added to stir for 12 hours. To the reaction mixture, methylene chloride (20 ml) was added to obtain an organic layer which was dried over anhydrous sodium sulfate, and the solvent was distilled out in vacuo. The residue was separated and purified by silicagel chromatography (ethyl acetate:hexane=1:2). To the reaction product in methanol (2 ml), water (0.3 ml) and 10%-palladium carbon (50 mg) were added to stir for 30 minutes at room temperature under hydrogen atmosphere. The pH of the resulting solution was adjusted to 7.0 by adding 0.1N sodium hydroxide solution and further stirred for 24 hours under hydrogen atmosphere. The reaction solution was filtrated with a celite (Johns Manville Sales Corp.), and then the solvent was distilled out in vacuo. The residue was dissolved into water (5 ml), treated with cation exchange resin [WK-10 Na +type, "Diaion" (trademark), 1×5cm], and lyophilized to afford the titled compound (44 mg).

Mass spectrum ($FAB^+$) m/z:
732.9 $(M+H)^+$.
$^1$H-NMR (270 MHz) spectrum ($D_2O$) δppm:
0.97 (3H, d, J=6.7 Hz, $CH_3$),
0.99 (3H, d, J=6.7 Hz, $CH_3$),
1.9–2.0 (1H, m, $Me_2CH$),
3.55 (1H, dd, J=6.7, 9.4 Hz, $Me_2CHCHaHb$),
3.75 (1H, dd, J=6.7, 9.4 Hz, $Me_2CHCHaHb$),
3.9–4.0 (1H, m, H5),
3.9–4.0 (1H, m, H 6'),
4.0–4.1 (1H, m, H6),
4.2–4.3 (1H, m, H3),
4.2–4.3 (1H, m, H2),
4.61 (1H, d, J=6.9 Hz, H1),
4.63 (1H, dd, J=2.0, 8.9 Hz, H4).
$^{13}$C-NMR (68 MHz) spectrum ($D_2O$) δppm:
20.7 ($CH_3$ ),
29.8 ($Me_2CH$),
65.8 (C6),
75.0 (C4),
76.3 (C5),
76.7 (C2),
77.6 (C3),
79.3 ($Me_2CHCH_2$),
104.4 (C1).

EXAMPLE 13

Octasodium 2-propylpentyl β-D-galactopyranoside 2,3,4,6-tetranhosphate

By treating as described in Example 12 excepting that 2-propylpentyl β-D-galactopyranoside (100 mg), 1H-tetrazol (285 mg) and dibenzyloxy (diisopropylamino) phosphine (939 mg) were selected, the titled compound (149 mg) was obtained.

Mass spectrum ($FAB^+$) m/z:
788.9 $(M+H)^+$.
$^1$H-NMR (270 MHz) spectrum ($D_2O$) δppm:
0.93 (6H, t, J=6.4 Hz, $CH_3$),
1.3–1.5 (8H, m, $CH_2CH_2$),
1.7–1.8 (1H, m, $Pr_2CH$),
3.64 (1H, dd, J=6.4, 9.4 Hz, $Pr_2CHCHaHb$),
3.89 (1H, dd, J=6.4, 9.4 Hz, $Pr_2CHCHaHb$),
3.9–4.0 (1H, m, H5),
4.0–4.1 (1H, m, H6'),
4.0–4.1 (1H, m, H6),
4.2–4.3 (1H, m, H3),
4.2–4.3 (1H, m, H2),
4.57 (1H, dd, J=2.0, 8.0 Hz, H4),
4.58 (1H, d, J=7.4 Hz, H1).
$^{13}$C-NMR (68 MHz) spectrum ($D_2O$) δppm:
15.9 ($CH_3$),
21.2 ($CH_2CH_2CH_3$),
34.4 ($CH_2CH_2CH_3$),
39.0 ($Pr_2CH$),
66.2 (C6),
74.9 (C4),
76.2 ($Pr_2CHCH_2$),
76.7 (C2),
76.8 (C5),
77.8 (C3),
104.8 (C1).

EXAMPLE 14

Octasodium 2-tetradecylhexadecyl β-D-galactopyranoside2,3,4,6-tetraphosphate

By treating as described in Example 12 excepting that 2-tetradecylhexadecyl β-D-galactopyranoside (100 mg), 1H-tetrazol (140 mg) and dibenzyloxy (diisopropylamino) phosphine (460 mg) were selected, the titled compound (69 mg) was obtained.

Mass spectrum ($FAB^+$) m/z:
1097.3 $(M+H)^+$.
$^1$H-NMR (270 MHz) spectrum ($D_2O$) δppm:
0.9–1.0 (6H, m, $CH_3$),
1.2–1.5 (52H, m, $CH_2$),
1.7–1.8 [(1H, m, $(C_{14}H_{29})_2CH$)],
3.5–3.6 (1H, m, $(C_{14}H_{29})_2CHCHaHb$),
3.8–4.0 (1H, m, $(C_{14}H_{29})_2CHCHaHb$),
3.9–4.0 (1H, m, H5),
3.9–4.0 (1H, m, H6'),
4.0–4.1 (1H, m, H6),
4.2–4.3 (1H, m, H3),
4.2–4.3 (1H, m, H2), 4.6–4.7 (1H, m, H1),
4.6–4.7 (1H, m, H4).
$^{13}$C-NMR (68 MHz) spectrum (D$_2$O) δppm:
15.9 (CH$_3$),
24–32 (CH$_2$),
39.6 [(C$_{14}$H$_{29}$)$_2$CH],
64.6 (C6),
74.6 (C4),
75.4 (C5),
76.7 (C2),
76.9 [(C$_{14}$H$_{29}$)$_2$CHCH$_2$],
77.6 (C3),
104.7 (C1).

EXAMPLE 15

Tetrasodium 2-methylpropyl β-D-galactopyranoside 3,4-diphosphate

To 2-methylpropyl β-D-galactopyranoside in acetone (20 ml), 97% sulfuric acid (10 μl) was added to stir for 18 hours under argon atmosphere. The reaction solution was neutralized by adding sodium carbonate, filtrated, and the solvent was distilled out in vacuo. The residue was purified by silica-gel chromatography (ethyl acetate hexane=3:2). To the reaction product in N,N-dimethylformamide (2 ml), sodium hydride (73.5 mg) was added, and then, benzyl bromide (218 μl) was added thereto under ice cooling to stir for 2 hours at room temperature under argon atmosphere. Under ice cooling, methanol (1 ml) and chloroform (10 ml) were added to the resulting solution which was washed by water, dried over anhydrous sodium sulfate, and then the solvent was distilled out in vacuo. The reaction product was purified by silica-gel chromatography (ethyl acetate:hexane 1:5). To the purified reaction product in methylene chloride (3 ml), 90% trifluoroacetic acid (0.8 ml) was added, which was stirred for 1 hour under ice cooling, and then the solvent was distilled out in vacuo. The residue and 1H-tetrazol (82 mg) were suspended in a mixture of dichloromethane and acetonitoril (1:1, 4 ml), and then dibenzyloxy (diisopropylamino) phosphine (539 mg) was added to stir for 12 hours at room temperature under argon atmosphere. To the reaction mixture, water (10 ml), ruthenium chloride 1 mg) and sodium periodate (334 mg) were added to stir for 12 hours. By adding methylene chloride (20 ml) into the reaction solution, an organic layer was obtained and dried over anhydrous sodium sulfate, and then the solvent was distilled out in vacuo. The residue was purified by silica-gel chromatography (ethyl acetate:hexane=1:1). To the resulting product in methanol (3 ml), water (0.5 ml) and 10%-palladium carbon (50 mg) were added to stir for 30 minutes under hydrogen atmosphere. Resulting solution was neutralized by 0.1N sodium hydroxide solution, stirred for 24 hours at room temperature under hydrogen atmosphere, filtrated with a celite, and then the solvent was distilled out in vacuo. The residue was dissolved into water (5 ml) and treated with a cation exchange resin [WK-10 Na$^+$ type "Diaion" (trademark) 1×5cm], and lyophilized to afford the titled compound (124 mg).

Mass spectrum (FAB$^+$) m/z:
485.0 (M+H)$^+$.
$^1$H-NMR (270 MHz) spectrum (D$_2$O) δppm:
0.96 (3H, d, J=6.9 Hz, CH$_3$),
1.9–2.0 (1H, m, Me$_2$CH),
3.50 (1H, dd, J=6.9, 9.4 Hz, Me$_2$CHCHaHb),
3.63 (1H, dd, J=6.9, 9.4 Hz, Me$_2$CHCHaHb),
3.6–3.7 (1H, m, H2),
3.6–3.7 (1H, m, H6'),
3.7–3.8 (1H, m, H6),
3.7–3.8 (1H, m, H5),
4.2–4.3 (1H, m, H3),
4.54 (1H, d, J=7.9 Hz, H1),
4.67 (1H, dd, J=3.0, 9.9 Hz, H4).
$^{13}$C-NMR (68 MHz) spectrum (D$_2$O) δppm:
20.5 (CH$_3$),
29.8 (Me$_2$CH),
61.5 (C6),
72.1 (C2),
72.6 (C4),
76.0 (C5),
78.0 (C3),
79.1 (Me$_2$CHCH$_2$),
104.8 (C1).

EXAMPLE 16

Tetrasodium 2-propylpentyl β-D-galactopyranoside 3,4-diphosphate

By treating as described in Example 15 excepting that 2-propylpentyl β-D-galactopyranoside (150 mg), 1H-tetrazol (74 mg) and dibenzyloxy (diisopropylamino) phosphine (485 mg) were selected, the titled compound (195 mg) was obtained.

Mass spectrum (FAB$^+$) m/z:
541.1 (M+H)$^+$.
$^1$H-NMR (270 MHz) spectrum (D$_2$O) δppm:
0.93 (6H, t, J=6.4 Hz, CH$_3$),
1.3–1.4 (8H, m, CH$_2$CH$_2$),
1.7–1.8 (1H, m, Pr$_2$CH),
3.62 (1H, dd, J=5.9, 9.9 Hz, Pr$_2$CHCHaHb),
3.74 (1H, dd, J=7.9, 9.4 Hz, H2),
3.7–3.8 (1H, m, H6'),
3.8–3.9 (1H, m, H5),
3.8–3.9 (1H, m, H6),
3.8–3.9 (1H, dd, J=5.9, 9.9 Hz, Pr$_2$CHCHaHb),
4.2–4.3 (1H, m, H3),
4.53 (1H, d, J=7.9 Hz, H1),
4.69 (1H, dd, J=2.0, 10.9 Hz, H4).
$^{13}$C-NMR (68 MHz) spectrum (D$_2$O) δppm:
15.7 (CH$_3$),
21.2 (CH$_2$CH$_2$CH$_3$),
34.6 (CH$_2$CH$_2$CH$_3$),
38.9 (Pr$_2$CH),
61.5 (C6),
72.0 (C2),
72.6 (C4),
75.8 (C5),
75.8 (Pr$_2$CHCH$_2$),
78.1 (C3),
105.0 (C1).

EXAMPLE 17

Tetrasodium 2-tetradecylhexadecyl β-D-galactopyranoside 3,4-dinhosphate

By treating as described in Example 15 excepting that 2-tetradecylhexadecyl β-D-galactopyranoside (200 mg), 1H-tetrazol (36 mg) and dibenzyloxy (diisopropylamino) phosphine (236 mg) were elected, the titled compound (103 mg) was obtained.

Mass spectrum (FAB$^+$) m/z:
849.4 (M+H)$^+$.
$^1$H-NMR (270 MHz) spectrum (D$_2$O) δppm:
0.9–1.0 (6H, m, CH$_3$),
1.2–1.5 (52H, m, CH$_2$),
1.8–1.9 (1H, m, (C$_{14}$H$_{29}$)$_2$CH),
3.4–3.5 (1H, m, (C$_{14}$H$_{29}$)$_2$CHCHaHb),
3.6–3.7 (1H, m, H5),
3.7–3.8 (1H, m, H2),
3.7–3.8 (1H, m, (C$_{14}$H$_{29}$)$_2$CHCHaHb),
3.7–3.8 (1H, m, H6'),
3.8–3.9 (1H, m, H6),
4.2–4.3 (1H, m, H3),
4.40 (1H, d, J=7.9 Hz, H1),
4.7–4.8 (1H, m, H4).
$^{13}$C-NMR (68 MHz) spectrum (D$_2$O) δppm:
15.8 (CH$_3$),
24–35 (CH$_2$),
39.8 [(C$_{14}$H$_{29}$)$_2$CH],
61.1 (C6),
72.1 (C2),
72.3 (C4),
75.7 [(C$_{14}$H$_{29}$)$_2$CHCH$_2$],
75.9 (C5),
78.0 (C3),
105.6 (C1).

EXAMPLE 18

Disodium 2-propylpentyl β-D-galactopyranoside 3-phosphate

To a mixture of 2-propylpentyl β-D-galactopyranoside (400 mg), di-n-butyl-tin oxide (341 mg) and benzene (20 ml), Molecular Sieves 4A (Linde Co., 400 mg,) was added to reflux the same for 18 hours, while removing moisture by a fractional distillation. To the reaction mixture, tetra-n-butylammonium iodide (505 mg) and 4-methoxybenzylchloride (463 μl) were added to further reflux for 4 hours and filtered, and then the solvent was distilled out in vacuo. The residue was purified by silica-gel chromatography (ethyl acetate:hexane=2:1). The resulting product was dissolved into N,N-dimethylformamide (3 ml), and sodium hydride (175 mg) was added thereto under ice cooling to stir for 30 minutes. To the reaction solution, benzyl bromide (519 μl) was added thereto with stirring under ice cooling, and then stirred for 4 hours at room temperature under argon atmosphere. To the reaction solution, methanol (1 ml) and chloroform (15 ml) were added under ice cooling, washed with water, and dried over anhydrous sodium sulfate, and then the solvent was distilled out in vacuo. The residue was purified by silica-gel chromatography (ethyl acetate:hexane=1:3). To the reaction product in methylene chloride (5 ml), 10% trifluoro acetic acid (5.0 ml) was added to stir for an hour under ice cooling, and then the solvent was distilled out in vacuo. The residue was purified by silica-gel chromatography (ethyl acetate:hexane=1:5). To a suspension of the reacting product and 1H-tetrazol (65 mg) in a mixture of dichloromethane and acetonitoril (1 1, 8 ml), dibenzyloxy (diisopropylamino) phosphine (430 mg) was added to stir for 12 hours at room temperature under argon atmosphere. Thereafter, water (15 ml), ruthenium chloride (1 mg) and sodium periodide (266 mg) were added thereto to stir for 12 hours. To the reaction solution, methylene chloride (20 ml) was added to obtain an organic layer, dried over anhydrous sodium sulfate, and then the solvent was distilled out in vacuo. The residue was purified by silica-gel chromatography (methyl acetate:hexane=1:5). To the reaction product in methanol (4 ml), water (0.5 ml) and 10%-palladium carbon (80 mg) were added to stir for 30 minutes at room temperature under argon The pH of the solution was adjusted to 7.0 by adding 0.1N sodium hydroxide solution to stir for 24 hours at room temperature under hydrogen atmosphere. The resulting solution was filtrated with celite (Johns Manville Sales Corp.), and then the solvent was distilled out in vacuo. The residue was dissolved into water (5 ml), treated a cation exchange resin [WK-10 Na $^+$ type "Diaion" (trademark), 1×5cm], and lyophilized to afford the titled compound (145 mg).

Mass spectrum (FAB$^+$) m/z:
417.1 (M+H)$^+$.
$^1$H-NMR (270 MHz) spectrum (CD$_3$OD) δppm:
0.89 (6H, t, J=6.4 Hz, CH$_3$),
1.1–1.5 (8H, m, CH$_2$CH$_2$),
1.6–1.7 (1H, m, Pr$_2$CH),
3.53 (1H, t, J=5.9 Hz, H5),
3.62 (1H, dd, J=5.9, 9.9 Hz, Pr$_2$CHCHaHb),
3.69 (1H, dd, J=7.9, 9.4 Hz, H2),
3.7–3.8 (2H, m, H6, H6'),
3.8–3.9 (1H, dd, J=5.9, 9.9 Hz, Pr$_2$CHCHaHb),
4.01 (1H, ddd, J=9.4, 3.0, 8.4 Hz, H3),
4.09 (1H, d, J=3.0 Hz, H4),
4.24 (1H, d, J=7.9 Hz, H1).
$^{13}$C-NMR (68 MHz) spectrum (CD$_3$OD) δppm:
14.8 (CH$_3$),
20.9, 21.0, 34.7, 34.8 (CH$_2$),
39.2 (Pr$_2$CH),
62.6 (C6),
70.0 (C4),
72.3 (C2),
73.9 (Pr$_2$CHCH$_2$),
76.4 (C5),
78.0 (C3),
105.5 (C1).

EXAMPLE 19

Tetrasodium 2-propylpentyl β-D-glucopyranoside 2,3-diphosphate

To 2-propylpentyl β-D-glucopyranoside (600 mg) in tetrahydrofuran (2.4 ml), benzylaldehyde dimethyl acetal (1.5 ml) and conc. sulfuric acid (50 μl) were added to stir for 65 hours at room temperature. The reaction solution was filtrated after neutralization by adding sodium carbonate, and then the solvent was distilled out in vacuo. The residue was purified by silica-gel chromatography (chloroform:methanol=10:1). By treating as described in Example 15 excepting that a part of resulting compound (200 mg), 1H-tetrazol (110 mg) and dibenzyloxy (diisopropylamino) phosphine (726 mg) were employed, the titled compound was obtained (258 mg).

Mass spectrum (FAB$^+$) m/z:

541.1 (M+H)$^+$.

$^1$H-NMR (270 MHz) spectrum (D$_2$O) δppm:

0.92 (6H, t, J=6.4 Hz, CH$_3$), 1.2–1.5 (8H, m, CH$_2$CH$_2$), 1.6–1.8 (1H, m, Pr$_2$CH), 3.5–3.6 (1H, m, H5), 3.61 (1H, t, J=8.4Hz, H4), 3.65 (1H, dd, J=5.9, 9.9 Hz, Pr$_2$CHCHaHb), 3.75 (1H, dd, J=6.9, 9.9 Hz, H6), 3.79 (1H, dd, J=5.9, 9.9 Hz, Pr$_2$CHCHaHb), 3.82 (1H, dd, J=5.4, 9.9 Hz, m, H6'), 3.96 (1H, dd, J=7.9, 8.4 Hz, H2), 4.16 (1H, q, J=8.44 Hz, H3), 4.62 (1H, d, J=7.9 Hz, H1).

$^{13}$C-NMR (68 MHz) spectrum (D$_2$O) δppm:

15.8 (CH$_3$), 21.1, 21.2, 34.5, 34.6 (CH$_2$), 38.9 (Pr$_2$CH), 63.0 (C6), 72.3 (C4), 76.1 (Pr$_2$CHCH$_2$), 77.9 (C5), 78.5 (C2), 81.1 (C3), 104.1 (C1).

EXAMPLE 20

Hexasodium 2-propylpentyl δ-D-glucopyranoside 2, 3,4-triphosphate

To 2-propylpentyl β-D-glucopyranoside (10 mg) in tetrahydrofuran (2 ml), trimethylamine (52.4 μl) and trityl chloride (105 mg) were added to stir for 100 hours at room temperature. After distilled out the solvent in vacuo, the residue was purified by silica-gel chromatography (chloroform:methanol=10:1). By treating as described in Example 15 excepting that the resulting compound, 1H-tetrazol (46 mg) and dibenzyloxy (diisopropylamino) phosphine 302 mg) were selecting, the titled compound (147 mg) was obtained.

Mass spectrum (FAB$^+$) m/z:

665.0 (M+H)$^+$.

$^1$H-NMR (270 MHz) spectrum (D$_2$O) δppm:

0.92 (6H, t, J=6.4 Hz, CH$_3$), 1.3–1.5 (8H, m, CH$_2$CH$_2$), 1.7–1.8 (1H, m, Pr$_2$CH), 3.5–3.7 (1H, m, H5), 3.65 (1H, dd, J=6.4, 9.9 Hz, Pr$_2$CHCHaHb), 3.81 (1H, dd, J=6.4, 9.9 Hz, Pr$_2$CHCHaHb), 3.85 (1H, dd, J=2.0, 12.9 Hz, H6), 3.95 (1H, dd, J=4.0, 12.9 Hz, m, H6'), 4.04 (1H, dd, J=7.4, 9.4 Hz, H2), 4.10 (1H, q, J=9.4 Hz, H4), 4.31 (1H, q, J=9.4 Hz, H3), 4.66 (1H, d, J=7.4 Hz, H1).

$^{13}$C-NMR (68 MHz) spectrum (D$_2$O) δppm:

15.8 (CH$_3$ ), 21.1, 21.2, 34.5, 34.6 (CH$_2$), 38.8 (Pr$_2$CH), 62.8 (C6), 74.0 (C4), 76.1 (Pr$_2$CHCH$_2$), 77.5 (C5), 78.5 (C2), 80.6 (C3), 104.1 (C1).

EXAMPLE 21

Tetrasodium 2-propylpentyl O-β-D-galactopyranosyl-(1→4)-β-D-glucopyranoside 3',4'-diphosphate To 2-propylpentyl O-β-D-galactopyranosyl-(1→4)-β-D-glucopyranoside (200 mg) in a mixture of acetone and tetrahydrofuran (1:3, 80 ml), conc. sulfuric acid (30 μl) was added to stir for 24 hours at room temperature. After neutralized the reaction solution with triethylamine, the solvent was distilled out in vacuo after filtration. The residue was purified by silica-gel chromatography (methylene:acetone 1:1). The reaction product was dissolved into N,N-dimethylformamide (2 ml), and sodium hydride (106 mg) was added thereto under ice cooling to stir for 30 minutes. To the reaction mixture, benzyl bromide (284 μl) was added to stir under ice cooling, which was further stirred for 4 hours at room temperature under argon atmosphere. To the reaction solution, methanol (1 ml) and methylene chloride (10 ml) were added under ice cooling, washed with water and dried over anhydrous sodium sulfate, and then the solvent was distilled out in vacuo. The residue was purified by silica-gel chromatography (ethyl acetate:hexane=1:4). To the reaction product in methylene chloride (3 ml), 90% trifluoro acetic acid (0.8 ml) was added to stir for an hour under ice cooling, and then the solvent was distilled out in vacuo. The residue was purified by silica-gel chromatography (ethyl acetate hexane (1:5). By treating as described in Example 15 excepting that the resulting product (180 mg), 1H-tetrazol (84 mg) and dibenzyloxy (diisopropylamino) phosphine (277 mg) were selected, the titled compound (120 mg) was obtained.

Mass spectrum (FAB$^+$) m/z:

703.1 (M+H)$^+$.

$^1$H-NMR (270 MHz) spectrum (D$_2$O) δppm:

glucose H1 (4.36, 1H, d, J=7.9 Hz),

H2 (3.29, 1H, dd, J=7.9, 8.9 Hz),

H3 (3.5–3.7, 1H, m),

H4 (3.6–3.7, 1H, m),

H5 (3.4–3.6, 1H, m),

H6' (3.87, 1H, dd, J=4.5, 12.4 Hz),

H6 (3.94, 1H, dd, J=2.5, 12.4 Hz), galactose H1 (4.53, 1H, d, J=7.9 Hz),

H2 (3.7–3.8, 1H, m),

H3 (4.15, 1H, dt, J=3.0, 8.9 Hz),

H4 (4.57, 1H, d, J=3.0 Hz),

H5 (3.7–3.8, 1H, m),

H6,H6' (3.7–3.9, 2H, m), aglycon CH$_3$ (0.90, 6H, t, J=6.4 Hz),

CH$_2$ (1.2–1.4, 8H, m),

CH (1.6–1.7, 1H, m),

OCHaHb (3.4–3.6, 1H, m),

OCHaHb (3.7–3.9, 1H, m).

$^{13}$C-NMR (68 MHz) spectrum (D$_2$O) δppm:

glucose C1 (104.0),
C2 (74.2),
C3 (75.7),
C4 (80.2),
C5 (75.9),
C6 (61.4),
galactose C1 (104.4),
C2 (71.8),
C3 (76.2),
C4 (71.7),
C5 (75.5),
C6 (60.5),
aglycon CH$_3$ (14.6),
CH$_2$ (20.4, 33.9),
CH (38.3),
OCH$_2$ (74.5).

EXAMPLE 22

Tetrasodium 2-tetradecylhexadecyl O-β-D-galactopyranosyl-(1→4)-β-D-glucopyranoside 3',4'-diphosphate By treating as described in example 21 excepting that 2-tetradecylhexadecyl O-β-D-galactopyranosyl-(1→4)-β-D-glucopyranoside (150 mg) was selected, the titled compound (177 mg) was obtained.

Mass spectrum (FAB$^+$) m/z:
1012.0 (M+H)$^+$.
$^1$H-NMR (270 MHz) spectrum (D$_2$O) δppm:
glucose H1 (4.28, 1H, d, J=7.9 Hz),
H2 (3.26, 1H, t, J=7.9 Hz),
H3 (3.5–3.6, 1H, m),
H4 (3.6–3.7, 1H, m),
H5 (3.4–3.5, 1H, m),
H6, H6' (3.8–3.9, 2H, m),
galactose H1 (4.54, 1H, d, J=7.9 Hz),
H2 (3.6–3.8, 1H, m),
H3 (4.1–4.2, 1H, m),
H4 (4.5–4.7, 1H, m),
H5 (3.7–3.8, 1H, m),
H6, H6' (3.6–3.8, 2H, m),
aglycon CH$_3$ (0.87, 6H, t, J=6.4 Hz),
CH$_2$ (1.2–1.4, 52H, m),
CH (1.5–1.7, 1H, m),
OCHaHb (3.3–3.4, 1H, m),
OCHaHb (3.7–3.8, 1H, m).
$^{13}$C-NMR (68 MHz) spectrum (D$_2$O) δppm:
glucose C1 (103.9),
C2 (74.0),
C3 (75.5),
C4 (79.9),
C5 (75.6),
C6 (61.4),
galactose C1 (104.0),
C2 (71.3),
C3 (76.4),
C4 (71.7),
C5 (75.2),
C6 (60.8),
aglycon CH$_3$ (14.5),
CH$_2$ (23.3, 27.1, 30.2, 30.4, 30.5, 30.6, 31.1, 32.7),
CH (38.7),
OCH$_2$ (74.3).

EXAMPLE 23

Sodium 2-propylpentyl O-α-L-fucopyranosyl-(1→2)-β-D-galactopyranoside 3-sulfate (23-1) and disodium 2-propylpentyl O-α-L-fucopyranosyl-(1→2)-β-D-galactopyranoside 3-phosphate (23-2)

To a suspension of 2-propylpentyl-β-D-galactopyranoside (15.0 g) and benzylaldehyde methyl acetal (15.6 ml) in tetrahydrofuran (200 ml), conc. sulfuric acid (1 ml) was added to stir for 20 hours at room temperature. The reaction solution was neutralized by adding sodium carbonate, filtrated, and then the solvent was distilled out in vacuo. The residue was purified by silica-gel chromatography (ethyl acetate:hexane=1:2). The reaction product and di-n-butyl-tin oxide (5.89 g) in methanol (225 ml) was refluxed for hours, and then the solvent was distilled out in vacuo. To the residue in tetrahydrofuran (100 ml), tetra-n-butylammonium iodide (13.1 g) and 4-methoxibenzochloride (4.81 ml) were added to reflux for 4 hours, filtrated, and then the solvent was distilled out in vacuo. The residue was purified by silica-gel chromatography (ethyl acetate:hexane=1:3). A part of reaction product (2.50 g) and phenyl 2,3,4-tri-O-benzyl-1-thio-β-L-fucopyranoside (5.26 g) which was separately prepared, were dissolved into a mixture of toluene and methylene chloride (3:1, 40 ml), and Molecular Sieves 4A (Linde Co.) (12.5 g) was added to stir for 24 hours under argon atmosphere. The reaction solution was cooled at −20° C., and N-iodosuccinicimide (4.49 g) and trifluoromethane sulfonic acid (177 μl ) were added to stir for an hour. The reaction solution was neutralized by adding triethylamine, filtrated, added toluene (100 ml), washed with water, dried over anhydrous sodium sulfate, and then the solvent was distilled out in vacuo. The residue was purified by silica-gel chromatography (ethyl acetate:hexane=1:3). To a part of the reaction product (540 mg) in a mixture of methylene chloride and water (20:1, 5 ml), DDQ (134 mg) was added to stir for 2 hours at room temperature. The reaction solution was filtrated, and then the solvent was distilled out in vacuo. The residue was purified by silica-gel chromatography (ethyl acetate:hexane=2:5) to afford 2-propylpentyl O-(2,3,4-tri-O-benzyl α-L-fucopyranosyl-(1→2)-O-4,6-O-benzylidene-β-D-galactopyranoside (188 mg).

To the resulting 2-propylpentyl O-(2,3,4-tri-O-benzyl α-L-fucopyranosyl-(1→2)-O-4,6-O-benzylidene β-D-galactopyranoside (87.6 mg) in N,N-dimethylformamide (1 ml), a complex of sulfur trioxide and pyridine was added to stir for an hour at room temperature, and then methanol (2 ml), tetrahydrofuran (2 ml) and sodium methoxide (29.7 mg) were added to stir for an hour, and then the solvent was distilled out in vacuo. The residue was purified by silica-gel chromatography (chloroform:methanol=10:1). To the reaction product in a mixture of tetrahydrofuran and methanol (1:1, 2 ml), 20%-palladium carbon was added to stir for 16 hours at room temperature under hydrogen atmosphere. The reacting solution was filtrated, and then the solvent was distilled out in vacuo. The residue was dissolved into water (2 ml) and lyophilized to afford the titled compound of sodium 2-propylpentyl O-α-L-fucopyranosyl-(1→2)-β-D-galactopyranoside 3-sulfate (37.5 mg) was obtained by freeze drying. Furthermore, by treating as described in Example 12 excepting that 2-propylpentyl O-(2, 3,4-tri-O-benzyl α-L-fucopyranosyl)-(1→2)-O-4,6-O-benzylidene-β-D-glucopyranoside (82.5 mg) and dibenzyloxy (diisopropylamino) phosphine (71.5 mg) were selected, the other titled compound of disodium 2-propylpentyl O-α-L-fucopyranosyl-(1→2)-β-D-galactopyranoside 3-phosphate (41.4 mg) was obtained.

Compound 23-1
Mass spectrum (FAB$^-$) m/z:
517.2 (M−Na)$^-$.
$^1$H-NMR (270 MHz) spectrum (CD$_2$OD) δppm:
galactose H$^1$ (4.38, 1H, d, J=7.4 Hz),
H2 (3.89, 1H, dd, J=7.4, 9.4 Hz),
H3 (4.43, 1H, dd, J=9.4, 3.0 Hz),
H4 (4.25, 1H, d, J=3.0 Hz),
H5 (3.54, 1H, t, J=6.4 Hz),
H6, H6' (3.74, 2H, d, J=6.4 Hz),
fucose H1 (5.3–5.4, 1H, m),
H2 (3.7–3.8, 1H, m),
H3 (3.7–3.8, 1H, m),
H4 (3.6–3.7, 1H, m),
H5 (4.3–4.5, 1H, m),
6-CH$_3$ (1.18, 2H, d, J=6.4 Hz),
aglycon CH$_3$ (0.90, 6H, t, J=6.4 Hz),
CH$_2$ (1.2–1.4, 8H, m),
CH (1.5–1.6, 1H, m),
OCHaHb (3.41, 1H, dd, J=5.4, 9.9 Hz),
OCHaHb (3.82, 1H, dd, J=6.4, 9.9 Hz).
$^{13}$C-NMR (68 MHz) spectrum (CD$_3$OD) δppm:
galactose C1 (103.9),
C2 (74.0),
C3 (82.8),
C4 (68.9),
C5 (76.2),
C6 (62.3),
fucose C1 (100.0),
C2 (70.2),
C3 (71.6),
C4 (73.7),
C5 (67.5),
C6 (16.8).
aglycon CH$_3$ (14.8),
CH$_2$ (20.9, 21.1, 34.8, 34.9),
CH (39.4),
OCH$_2$ (73.8).

Compound 23-2
Mass spectrum (FAB$^+$) m/z:
563.2 (M+H)$^+$.
$^1$H-NMR (270 MHz) spectrum (CD$_3$OD) δppm:
galactose H1 (4.39, 1H, d, J=7.4 Hz),
H2 (3.7–3.9, 1H, m),
H3 (4.2–4.3, 1H, m),
H4 (4.1–4.2, 1H, m),
H5 (3.5–3.7, 1H, m),
H6, H6' (3.7–3.9, 2H, m),
fucose H1 (5.52, 1H, m),
H2 (3.7–3.9, 1H, m),
H3 (3.7–3.9, 1H, m), H4 (3.6–3.7, 1H, m),
H5 (4.3–4.5, 1H, m),
6-CH$_3$ (1.20, 2H, d, J=6.9 Hz),
aglycon CH$_3$ (0.90, 6H, t, J=6.4 Hz),
CH$_2$ (1.2–1.4, 8H, m),
CH (1.5–1.7, 1H, m),
OCHaHb (3.42, 1H, dd, J=5.4, 9.9 Hz),
OCHaHb (3.82, 1H, dd, J=6.4, 9.9 Hz).
$^{13}$C-NMR (68 MHz) spectrum (CD$_3$OD) δppm:
galactose C1 (103.7),
C2 (75.4),
C3 (78.9),
C4 (69.8),
C5 (76.0),
C6 (62.3),
fucose C1 (99.8),
C2 (69.5),
C3 (71.4),
C4 (73.6),
C5 (67.3),
C6 (16.8),
aglycon CH$_2$ (14.8),
CH$_2$ (20.7, 20.9, 34.5, 34.6),
CH (39.2),
OCH$_2$ (73.8).

EXAMPLE 24

Disodium 2-propylpentyl O-α-L-fucopyranosyl-(1→2)-β-D-galactopyranoside 3,3'-disulfate (24-1) and tetrasodium 2-propylpentyl O-α-L-fucopyranosyl-(1→2)-β-D-galactopyranoside 3,3'-diphosphate (24-2)

By treating as described in Example 23 excepting that 2-propylpentyl 4,6-O-benzylidene-3-O-(4-methoxybenzyl)-β-D-galactopyranoside (630 mg) and phenyl 2,4-di-O-benzyl-3-O-(4-methoxybenzyl)-1-thio-β-L-fucopyranoside (840 mg) were selected as a starting compound were selected, 2-propylpentyl O-(2,4-di-O-benzyl α-L-fucopyranosyl)-(1→2)-O-4,6-O-benzylidene-β-D-galactopyranoside (327 mg) was obtained. By treating as described in Example 23 excepting that the resulting compound (150 mg) and a complex of sulfur trioxide and pyridine (167 mg) were selected, the titled compound of disodium 2-propylpentyl O-α-L-fucopyranosyl-(1→2)-β-D-galactopyranoside 3,3'-disulfate (112 mg) was obtained. Furthermore, by treating as described in Example 12 excepting that 2-propylpentyl O-(2,4-di-O-benzyl-α-L-fucopyranosyl)-(1→2)-O-4,6-O-benzylidene-β-D-galactopyranoside (150 mg) and dibenzyloxy (diisopropylamino) phosphine (293 mg) were selected as a starting compound were selected, the other titled compound of tetrasodium 2-propylpentyl O-α-L-fucopyranosyl-(1→2) -β-D-galactopyranoside 3,3'-diphosphate (91.3 mg) was obtained.

Compound 24-1
Mass spectrum (FAB$^-$) m/z:
619.1 (M−Na)$^-$.
$^1$H-NMR (270 MHz) spectrum (CD$_3$OD) δppm:
galactose H1 (4.41, 1H, d, J=6.9 Hz),
H2 (3.93, 1H, dd, J=6.9, 9.9 Hz), H3 (4.46, 1H, dd, J=9.9, 3.0 Hz),
H4 (4.29, 1H, d, J=3.0 Hz),
H5 (3.54, 1H, t, J=5.9 Hz),
H6, H6' (3.74, 2H, d, J=5.9 Hz),
fucose H1 (5.36, 1H, d, J=4.0 Hz),
H2 (3.95, 1H, dd, J=4.0, 9.9 Hz),
H3 (4.49, 1H, dd, J=9.9, 3.0 Hz),
H4 (4.05, 1H, d, J=3.0 Hz),
H5 (4.4–4.5, 1H, m),
6-CH$_3$ (1.19, 2H, d, J=6.4 Hz),
aglycon CH$_3$ (0.90, 6H, t, J=6.4 Hz),
CH$_2$ (1.2–1.5, 8H, m),
CH (1.5–1.7, 1H, m),
OCHaHb (3.45, 1H, dd, J=4.9, 9.4 Hz),
OCHaHb (3.80, 1H, dd, J=6.9, 9.4 Hz).
$^{13}$C-NMR (68 MHz) spectrum (CD$_3$OD) δppm:
galactose C1 (103.7),
C2 (73.9),
C3 (82.8),
C4 (68.9),
C5 (76.2),
C6 (62.3),
fucose C1 (100.3),
C2 (68.0),
C3 (79.2),
C4 (72.0),
C5 (67.4),
C6 (16.8),
aglycon CH$_3$ (14.9),
CH$_2$ (20.8, 21.1, 34.7, 34.9),
CH (39.4),
OCH$_2$ (73.8).
Compound 24-2
Mass spectrum (FAB$^+$) m/z:
687.1 (M+H)$^+$.
$^1$H-NMR (270 MHz) spectrum (CD$_3$OD) δppm:
galactose H1 (4.43, 1H, d, J=7.9 Hz),
H2 (3.7–3.8, 1H, m),
H3 (4.2–4.3, 1H, m),
H4 (4.1–4.2, 1H, m),
H5 (3.5–3.7, 1H, m),
H6, H6' (3.7–3.9, 2H, m),
fucsoe H1 (5.43, 1H, d, J=4.0 Hz),
H2 (3.9–4.0, 1H, m),
H3 (4.2–4.3, 1H, m),
H4 (3.9–4.0, 1H, m),
H5 (4.3–4.4, 1H, m),
6-CH$_3$ (1.20, 2H, d, J=6.4 Hz),
aglycon CH$_3$ (0.87, 6H, t, J=6.9 Hz),
CH$_2$ (1.1–1.5, 8H, m),
CH (1.5–1.7, 1H, m),
OCHaRb (3.50, 1H, dd, J=5.4, 9.9 Hz),
OCHaHb (3.78, 1H, dd, J=6.4, 9.9 Hz).
$^{13}$C-NMR (68 MHz) spectrum (CD$_3$OD) δppm:
galactose C1 (103.1),
C2 (76.0),
C3 (78.5),
C4 (69.4),
C5 (75.4),
C6 (62.0),
fucose C1 (99.9),
C2 (68.7),
C3 (74.6),
C4 (72.4),
C5 (67.1),
C6 (16.8),
aglycon CH$_3$ (14.7),
CH$_2$ (20.2, 20.5, 33.9, 34.1),
CH (38.7),
OCH$_2$ (74.5).

EXAMPLE 25

Disodium 2-propylpentyl O-α-L-fucopyranosyl-(1→2)-β-D-galactonyranoside 3,6-disulfate By treating as described in Example 2 excepting that sodium 2-propylpentyl O-α-L-fucopyranosyl-(1→2)-β-D-galactopyranoside -3-sulfate (20.0 mg) obtained by Example 23 and a complex of sulfurous acid and trimethyl ammonium (6.2 mg) were selected, the titled compound (12.1 mg) was obtained.

Mass spectrum (FAB$^-$) m/z:
619.1 (M−Na)$^-$.
$^1$H-NMR (270 MHz) spectrum (DMSO-d$_6$) δppm:
galactose H1 (4.39, 1H, d, J=7.4 Hz),
H2 (3.89, 1H, dd, J=7.4, 9.4 Hz),
H3 (4.44, 1H, dd, J=9.4, 3.0 Hz),
H4 (4.30, 1H, d, J=3.0 Hz),
H5 (3.75, 1H, t, J=6.4 Hz),
H6, H6' (4.06, 2H, d, J=6.4 Hz),
fucose H1 (5.3–5.4, 1H, m),
H2 (3.7–3.8, 1H, m),
H3 (3.7–3.8, 1H, m),
H4 (3.6–3.7, 1H, m),
H5 (4.3–4.5, 1H, m),
6-CH$_3$ (1.18, 2H, d, J=6.4 Hz),
aglycon CH$_3$ (0.90, 6H, t, J=6.4 Hz),
CH$_2$ (1.2–1.4, 8H, m),
CH (1.5–1.6, 1H, m),
OCHaHb (3.4–3.5, 1H, m),
OCHaHb (3.8–3.9, 1H, m).
$^{13}$C-NMR (68 MHz) spectrum (DMSO-d$_6$) δppm:
galactose C1 (104.1),
C2 (73.9),
C3 (83.0),
C4 (69.2),
C5 (74.1),
C6 (66.7),
fucose C1 (100.2),
C2 (70.3),
C3 (71.8),
C4 (73.7),
C5 (67.5),
C6 (16.8),
aglycon CH$_3$ (14.8),
CH$_2$ (21.0, 21.1, 34.8, 35.0),
CH (39.4),
OCH$_2$ (73.9).

EXAMPLE 26

Trisodium 2-propylpentyl O-α-L-fucopyranosyl-(1→2)-β-D-galactopyranoside 3,3',6-trisulfate By treating as described in Example 2 excepting that disodium 2-propylpentyl O-α-L-fucopyranosyl-(1→2)-β-D- galactopyranoside 3,3'-disulfate (40.0 mg) obtained by the Example 24 and a complex of sulfurous acid and trimethyl ammonium (10.4 mg) were selected, the titled compound (25.1 mg) was obtained.

Mass spectrum (FAB$^-$) m/z:
721.0 (M–Na)$^-$.
$^1$H-NMR (270 MHz) spectrum (DMSO-d$_6$) δppm:
galactose H1 (4.41, 1H, d, J=7.8 Hz),
H2 (3.89, 1H, dd, J=7.8, 9.4 Hz),
H3 (4.45, 1H, dd, J=9.4, 3.0 Hz),
H4 (4.30, 1H, d, J=3.0 Hz),
H5 (3.77, 1H, t, J=6.8 Hz),
H6, H6' (4.07, 2H, d, J=6.8 Hz),
fucose H1 (5.39, 1H, d, J=4.0 Hz),
H2 (3.94, 1H, dd, J=4.0, 9.9 Hz),
H3 (4.49, 1H, dd, J=9.9, 3.0 Hz),
H4 (4.06, 1H, d, J=3.0 Hz),
H5 (4.4–4.5, 1H, m),
6-CH$_3$ (1.19, 2H, d, J=6.4 Hz),
aglycon CH$_3$ (0.90, 6H, t, J=6.4 Hz),
CH$_2$ (1.2–1.4, 8H, m),
CH (1.5–1.6, 1H, m),
OCHaHb (3.4–3.5, 1H, m),
OCHaHb (3.8–3.9, 1H, m).
$^{13}$C-NMR (68 MHz) spectrum (DMSO-d$_6$) δppm:
galactose C1 (104.2),
C2 (74.0),
C3 (82.7),
C4 (69.3),
C5 (74.1),
C6 (66.7),
fucose C1 (100.4),
C2 (68.1),
C3 (79.4),
C4 (72.1),
C5 (67.5),
C6 (16.9),
aglycon CH$_3$ (14.9),
CH$_2$ (21.0, 21.1, 34.8, 34.9),
CH (39.4),
OCH$_2$ (73.9).

EXAMPLE 27

Sodium 2-tetradecylhexadecyl O-α-L-fucopyranosyl-(1→2)-β-D-galactopyranoside 3-sulfate (27-1) and disodium 2-tetradecylhexadecyl O-α-L-fucopyranosyl-(1→2)-β-D-galactopyranoside 3-phosphate (27-2)

By treating as described in Example 23 excepting that 2-tetradecylhexadecyl β-D-galactopyranoside (6.5 g) was selected as a starting compound, the titled compound of sodium 2-tetradecylhexadecyl O-α-L-fucopyranosyl-(1→2)-β-D-galactopyranoside 3-sulfate (50.0 mg) and disodium 2-tetradecylhexadecyl O-α-L-fucopyranosyl-(1→2)-β-D-galactopyranoside 3-phosphate (60.8 mg) were obtained.

Compound 27-1
Mass spectrum (FAB$^-$) m/z:
825.5 (M–Na)$^-$.
$^1$H-NMR (270 MHz) spectrum (CD$_3$OD) δppm:
galactose H1 (4.4–4.5, 1H, m),
H2 (3.8–3.9, 1H, m),
H3 (4.4–4.5, 1H, m),
H4 (4.33, 1H, d, J=4.0 Hz),
H5 (3.6–3.7, 1H, m),
6, H6' (3.7–3.9, 2H, m),
fucose H1 (5.2–5.3, 1H, m),
H2 (3.7–3.8, 1H, m),
H3 (3.7–3.8, 1H, m),
H4 (3.6–3.8, 1H, m),
H5 (4.3–4.4, 1H, m),
6-CH$_3$ (1.18, 2H, d, J=6.4 Hz),
aglycon CH$_3$ (0.90, 6H, t, J=6.9 Hz),
CH$_2$ (1.3–1.4, 8H, m),
CH (1.5–1.7, 1H, m),
OCHaHb (3.4–3.5, 1H, m),
OCHaHb (3.7–3.8, 1H, m).
$^{13}$C-NMR (68 MHz) spectrum (CD$_3$OD) δppm:
galactose C1 (103.2),
C2 (74.6),
C3 (82.5),
C4 (67.9),
C5 (75.0),
C6 (61.2),
fucose C1 (100.0),
C2 (69.7),
C3 (71.3),
C4 (74.4),
C5 (67.5),
C6 (16.9),
aglycon CH$_3$ (14.7),
CH$_2$ (23.6, 27.2, 27.5, 30.4, 30.6, 30.7, 30.8, 30.9, 31.7, 32.9),
CH (39.3),
OCH$_2$ (74.2).
Compound 27-2
Mass spectrum (FAB$^+$) m/z:
871.5 (M+H)$^+$.
$^1$H-NMR (270 MHz) spectrum (D$_2$O) δppm:
galactose H1 (4.3–4.5, 1H, m),
H2 (3.6–3.8, 1H, m),
H3 (4.2–4.3, 1H, m),
H4 (4.1–4.2, 1H, m),
H5 (3.5–3.6, 1H, m),
H6, H6' (3.6–3.8, 2H, m),
fucose H1 (5.3–5.4, 1H, m),
H2 (3.7–3.8, 1H, m),
H3 (3.8–3.9, 1H, m),
H4 (3.6–3.8, 1H, m),
H5 (4.2–4.3, 1H, m),
6-CH$_3$ (1.14, 2H, d, J=6.4 Hz),
aglycon CH$_3$ (0.84, 6H, t, J=6.9 Hz),
CH$_2$ (1.1–1.4, 8H, m),
CH (1.4–1.6, 1H, m),
OCHaHb (3.3–3.4, 1H, m),
OCHaHb (3.6–3.7, 1H, m).
$^{13}$C-NMR (68 MHz) spectrum (D$_2$O) δppm:
galactose C1 (103.0),
C2 (75.4),
C3 (78.9),
C4 (68.6), C5 (75.0),
C6 (61.2),
fucose C1 (99.7),
C2 (69.2),
C3 (71.0),
C4 (73.2),
C5 (67.1),
C6 (16.9),
aglycon $CH_3$ (14.6),
$CH_2$ (23.4, 27.0, 27.3, 30.2, 30.4, 30.5, 30.6, 30.7, 31.4, 32.8),
CH (39.2),
$OCH_2$ (73.8).

EXAMPLE 28

Disodium -2-tetradecylhexadecyl O-α-L-fucopyranosyl-(1→2)-β-D-galactopyranoside 3,3'-disulfate (28-1) and tetrasodium 2-tetradecylhexadecyl O-α-L-fucopyranosyl-(1→2)-β-D-galactopyranoside 3,3'-diphosphate (28-2)

By treating as described in Example 24 excepting that 2-tetradecylhexadecyl β-D-galactopyranoside (6.5 g) was selected, the titled compound of disodium 2-tetradecylhexadecyl O-α-L-fucopyranosyl-(1→2)-β-D-galactopyranoside 3,3'-disulfate (78.0 mg) and tetrasodium 2-tetradecylhexadecyl O-α-L-fucopyranosyl-(1→2)-β-D-galactopyranoside 3,3'-diphosphate (11.2 mg) were obtained.

Compound 28-1
Mass spectrum (FAB⁻) m/z:
927.5 (M−Na)⁻.
$^1$H-NMR (270 MHz) spectrum ($CD_3OD$) δppm:
galactose H1 (4.5–4.6, 1H, m),
H2 (3.7–3.8, 1H, m),
H3 (4.5–4.6, 1H, m),
H4 (4.3–4.4, 1H, m),
H5 (3.6–3.7, 1H, m),
H6, H6' (3.6–3.8, 2H, m),
fucose H1 (5.2–5.3, 1H, m),
H2 (3.9–4.0, 1H, m),
H3 (4.5–4.6, 1H, m),
H4 (4.0–4.2, 1H, m),
H5 (4.3–4.4, 1H, m),
6-$CH_3$ (1.22, 2H, d, J=6.4 Hz),
aglycon $CH_3$ (0.89, 6H, t, J=6.4 Hz),
$CH_2$ (1.2–1.4, 8H, m),
CH (1.5–1.7, 1H, m),
OCHaHb (3.4–3.5, 1H, m),
OCHaHb (3.6–3.7, 1H, m).
$^{13}$C-NMR (68 MHz) spectrum ($CD_3OD$) δppm:
galactose C1 (103.0),
C2 (75.4),
C3 (82.3),
C4 (67.6),
C5 (74.7),
C6 (60.9),
fucose C1 (100.5),
C2 (67.5),
C3 (79.0),
C4 (71.4),
C5 (67.4),
C6 (16.7),
aglycon $CH_3$ (14.7),
$CH_2$ (23.6, 26.9, 27.3, 30.3, 30.5, 30.6, 30.7, 31.4, 31.7, 32.9),
CH (39.2),
$OCR_2$ (74.3).
Compound 28-2
Mass spectrum (FAB⁺) m/z:
995.5 (M+H)⁺.
$^1$-NMR (270 MHz) spectrum ($D_2O$) δppm:
galactose H1 (4.5–4.6, 1H, m),
H2 (3.9–4.1, 1H, m),
H3 (4.0–4.1, 1H, m),
H4 (3.9–4.0, 1H, m),
H5 (3.5–3.7, 1H, m),
H6, H6' (3.6–3.8, 2H, m),
fucose H1 (4.8–4.9, 1H, m),
H2 (3.6–3.7, 1H, m),
H3 (4.2–4.3, 1H, m),
H4 (3.9–4.1, 1H, m),
H5 (4.1–4.3, 1H, m),
6-$CH_3$ (1.30, 2H, d, J=6.4 Hz),
aglycon $CH_3$ (0.89, 6H, t, J=6.4 Hz),
$CH_2$ (1.2–1.4, 8H, m),
CH (1.5–1.7, 1H, m),
OCHaHb (3.4–3.5, 1H, m),
OCHaHb (3.6–3.7, 1H, m).
$^{13}$C-NMR (68 MHz) spectrum ($D_2O$) δppm:
galactose C1 (103.7),
C2 (74.5),
C3 (78.4),
C4 (71.3),
C5 (74.4),
C6 (60.7),
fucose C1 (100.7),
C2 (71.2),
C3 (76.2),
C4 (71.5),
C5 (68.1),
C6 (16.6),
aglycon $CH_3$ (14.5),
$CH_2$ (23.4, 26.9, 27.1, 30.2, 30.3, 30.4, 30.6, 31.1, 31.2, 32.7),
CH (38.8),
$OCH_2$ (73.6).

EXAMPLE 29

Disodium 2-tetradecylhexadesyl O-α-L-fuconyranosyl-(1→2)-β-D-galactopyranoside 3,6-disulfate By treating as described in Example 2 excepting that sodium 2-tetradecylhexadecyl O-α-L-fucopyranosyl-(1→2)-β-D-galactopyranoside 3-sulfate (20.0 mg) obtained by Example 27 and a complex of sulfurous acid and trimethyl ammonium (4.0 mg) were selected, the titled compound (10.0 mg) was obtained.

Mass spectrum (FAB⁻) m/z:
927.5 (M−Na)⁻.
$^1$H-NMR (270 MHz) spectrum ($CD_3OD$) δppm:

galactose H1 (4.4–4.5, 1H, m),
H2 (3.8–3.9, 1H, m),
H3 (4.4–4.5, 1H, m),
H4 (4.33, 1H, d, J=4.0 Hz),
H5 (3.8–3.9, 1H, m),
H6, H6' (4.0–4.2, 2H, m),
fucose H1 (5.2–5.3, 1H, m),
H2 (3.7–3.8, 1H, m),
$^1$H3 (3.7–3.8, 1H, m),
H4 (3.6–3.8, 1H, m),
H5 (4.3–4.4, 1H, m),
6-CH$_3$ (1.18, 2H, d, J=6.4 Hz),
aglycon CH$_3$ (0.90, 6H, t, J=6.9 Hz),
CH$_2$ (1.3–1.4, 8H, m),
CH (1.5–1.7, 1H, m),
OCHaHb (3.4–3.5, 1H, m),
OCHaHb (3.7–3.8, 1H, m).
$^3$C-NMR (68 MHz) spectrum (CD$_3$OD) δppm:
galactose C1 (103.3),
C2 (74.6),
C3 (82.6),
C4 (68.1),
C5 (72.9),
C6 (65.7),
fucose C1 (100.1),
C2 (69.9),
C3 (71.3),
C4 (74.4),
C5 (67.5),
C6 (16.8),
aglycon CH$_3$ (14.7),
CH$_2$ (23.6, 27.4, 27.5, 30.5, 30.6, 30.7, 30.8, 30.9, 31.7, 32.9),
CH (39.3),
OCR$_2$ (74.2).

EXAMPLE 30

Trisodium 2-tetradecylhexadecyl O-α-L-fucopyranosyl-(1→2)-β-D-galactopyranoside 3,3',6-trisulfate By treating as described in Example 2 excepting that disodium 2-tetradecylhexadecyl O-α-L-fucopyranosyl-(1→2)-β-D-galactopyranoside 3,3'-disulfate (40.0 mg) obtained by the Example 28 and a complex of sulfurous acid and trimethyl ammonium (7.1 mg) were selected, the titled compound (23.2 mg) was obtained.

Mass spectrum (FAB$^-$) m/z:
1029.4 (M–Na)$^-$.
$^1$H-NMR (270 MHz) spectrum (CD$_3$OD) δppm:
galactose H1 (4.4–4.5, 1H, m),
H2 (3.8–3.9, 1H, m),
H3 (4.4–4.5, 1H, m),
H4 (4.3–4.4, 1H, m),
H5 (3.8–3.9, 1H, m),
H6, H6' (3.9–4.2, 2H, m),
fucose H1 (5.2–5.3, 1H, m),
H2 (3.9–4.0, 1H, m),
H3 (4.5–4.6, 1H, m),
H4 (4.0–4.2, 1H, m),
H5 (4.3–4.4, 1H, m),
6-CH$_3$ (1.20, 2H, d, J=6.4 Hz),
aglycon CH$_3$ (0.89, 6H, t, J=6.9 Hz),
CH$_2$ (1.3–1.4, 8H, m),
CH (1.5–1.7, 1H, m),
OCHaHb (3.4–3.5, 1H, m),
OCHaHb (3.7–3.8, 1H, m).
$^{13}$C-NMR (68 MHz) spectrum (CD$_3$OD) δppm:
galactose C1 (103.2),
C2 (74.7),
C3 (82.6),
C4 (68.3),
C5 (72.9),
C6 (65.9),
fucose C1 (100.4),
C2 (67.5),
C3 (79.1),
C4 (71.6),
C5 (67.4),
C6 (16.8),
aglycon CH$_3$ (14.8),
CH$_2$ (23.5, 27.4, 27.5, 30.4, 30.6, 30.7, 30.8, 30.9, 31.7, 32.9),
CH (39.3),
OCH$_2$ (74.3).

EXAMPLE 31

Sodium 2-tetradecylhexadecyl β-D-galactopyranoside 3-sulfate

By treating as described in Example 1 excepting that 2-tetradecylhexadecyl β-D-galactopyranoside (250 mg) and a complex of sulfurous acid and trimethyl ammonium (69.5 mg) were selected, the titled compound (198 mg) was obtained.

Mass spectrum (FAB$^-$) m/z:
679.5 (M–Na)$^-$, 701.5 (M–E)$^-$.
$^1$H-NMR (270 MHz) spectrum (CD$_3$OD) δppm:
0.90 (6H, t, J=6.8 Hz, CH),
1.3 (52H, s, CH$_2$),
1.5–1.7 (1H, m, (C$_{14}$H$_{29}$)$_2$CH),
3.42 (1H, dd, J=6.4, 9.8 Hz, (C$_{14}$H$_{29}$)$_2$CHCHaHb),
3.53 (1H, t, J=6.4 Hz, H5),
3.70 (1H, dd, J=7.8, 9.3 Hz, H2),
3.74 (2H, d, J=6.4 Hz, H6,H6'),
3.80 (1H, dd, J=6.4, 9.3 Hz, (C$_{14}$H$_{29}$)$_2$CHCHaHb),
4.21 (1H, dd, J=3.4, 9.3 Hz, H3),
4.25 (1H, d, J=3.4 Hz, H4),
4.28 (1H, d, J=7.8 Hz, H1).
$^{13}$C-NMR (68 MHz) spectrum (CD$_3$OD) δppm:
14.4 (CH$_3$),
23.6, 27.6, 27.7, 30.3, 30.6, 31.0, 32.0, 32.9 (CH$_2$),
39.4 (CH),
62.2 (C6),
68.5 (C4),
70.7 (C2),
74.0 (OCH$_2$),
76.5 (C5),
82.2 (C3),
105.0 (C1).

EXAMPLE 32

Disodium 2-tetradecylhexadecyl β-D-galactopyranoside 3,6-disulfate

By treating as described in Example 1 excepting that 2-tetradecylhexadecyl β-D-galactopyranoside (250 mg) and a complex of sulfurous acid and trimethyl ammonium (127 mg) were selected, the titled compound (221 mg) was obtained.

Mass spectrum (FAB$^-$) m/z:
781.4 (M–Na)$^-$, 803.4 (M–H)$^-$.
$^1$H-NMR (270 MHz) spectrum (CD$_3$OD—D$_2$O) δppm:
0.90 (6H, t, J=6.8 Hz, CH$_3$),
1.30 (52H, s, CH$_2$),
1.5–1.7 (1H, m, (C$_{14}$H$_{29}$)$_2$CH),
3.41 (1H, dd, J=5.9, 9.8 Hz, (C$_{14}$H$_{29}$)$_2$CHCHaHb),
3.70 (1H, dd, J=7.8, 9.3 Hz, H2),
3.78 (1H, dd, J=6.4, 9.8 Hz, (C$_{14}$H$_{29}$)$_2$CHCHaHb),
3.82 (1H, dd, J=6.4, 6.1 Hz, H5),
4.16 (1H, dd, J=6.4, 10.3 Hz, H6),
4.22 (1H, dd, J=6.1, 10.3 Hz, H6'),
4.25 (1H, d, J=9.3 Hz, H3),
4.27 (1H, s, H4),
4.30 (1H, d, J=7.8 Hz, H1).
$^{13}$H-NMR (68 MHz) spectrum (CD$_3$OD—H$_2$O) δppm:
14.7 (CH$_3$),
23.6, 27.2, 30.4, 30.6, 30.8, 30.9, 31.1, 32.9 (CH$_2$),
38.8 (CH),
66.3 (C6),
67.2 (C4),
69.9 (C2),
72.6 (C5),
74.6 (OCH$_2$),
81.3 (C3),
104.3 (C1).

EXAMPLE 33

Trisodium 2-tetradecylhexadecyl β-D-galactopyranoside 3,4,6-trisulfate (33-1) and tetrasodium 2-tetradecylhexadecyl β-D-galactopyranoside 2,3,4,6-tetrasulfate (33-2)

By treating as described in Example 2 excepting that sodium 2-tetradecylhexadecyl β-D-galactopyranoside 3-sulfate (100 mg) obtained by Example 31 and a complex of sulfurous acid and trimethyl ammonium (105 mg) were selected, the titled compound of trisodium 2-tetradecylhexadecyl β-D-galactopyranoside 3,4,6-trisulfate (57 mg) and tetrasodium 2-tetradecylhexadecyl β-D-galactopyranoside 2,3,4,6-tetrasulfate (41 mg) were obtained.

Compound 33-1
Mass spectrum (FAB$^-$) m/z:
883.4 (M–Na)$^-$, 905.4 (M–H)$^-$.
$^1$H-NMR (270 MHz) spectrum (CD$_3$OD—D$_2$O) δppm:
0.84 (6H, t, J=6.8 Hz, CH$_3$),
1.30 (52H, s, CH$_2$),
1.5–1.7 (1H, m, (C$_{14}$H$_{29}$)$_2$CH),
3.42 (1H, dd, J=5.9, 9.3 Hz, (C$_{14}$H$_{29}$)$_2$CHCHaHb),
3.57 (1H, dd, J=8.4, 9.4 Hz, H2),
3.78 (1H, dd, J=6.4, 9.3 Hz, (C$_{14}$H$_{29}$)$_2$CHCHaHb),
4.00 (1H, dd, J=6.4, 4.9 Hz, H5),
4.18 (1H, dd, J=6.4, 10.9 Hz, H6),
4.23 (1H, dd, J=4.9, 10.9 Hz, H6'),
4.40 (1H, d, J=9.4 Hz, H3),
4.45 (1H, d, J=8.4 Hz, H1),
5.00 (1H, s, H4).
$^{13}$C-NMR (68 MHz) spectrum (CD$_3$OD—D$_2$O) δppm:
14.7 (CH$_3$),
23.6, 26.7, 27.0, 30.2, 30.5, 30.7, 30.9, 32.9 (CH$_2$), 38.6 (CH),
67.3 (C6),
70.0 (C2),
72.5 (C5),
75.1 (OCH$_2$),
75.8 (C4),
78.6 (C3),
104.1 (C1).

Compound 33-2
Mass spectrum (FAB$^-$) m/z:
985.3 (M–Na)$^-$.
$^1$H-NMR (270 MHz) spectrum (CD$_3$OD—D$_2$O) δppm:
0.88 (6H, t, J=6.8 Hz, CH$_3$),
1.28 (52H, s, CH$_2$),
1.6–1.7 (1H, m, (C$_{14}$H$_{29}$)$_2$CH),
3.48 (1H, dd, J=5.9, 9.3 Hz, (C$_{14}$H29)$_2$CHCHaHb),
3.80 (1H, dd, J=6.4, 9.3 Hz, (C$_{14}$H$_{29}$)$_2$CHCHaHb),
4.10 (1H, dd, J=6.9, 5.4 Hz, H5),
4.20 (1H, dd, J=6.9, 9.9 Hz, H6),
4.25 (1H, dd, J=5.4, 9.9 Hz, H6'),
4.40 (1H, dd, J=7.4, 9.4 Hz, H2),
4.55 (1H, dd, J=2.0, 9.4 Hz, H3),
4.60 (1H, d, J=7.4 Hz, H1),
5.10 (1H, d, J=2.0 Hz, H4).
$^{13}$H-NMR (68 MHz) spectrum (CD$_3$OD—D$_2$O) δppm:
14.7 (CH$_3$),
23.6, 26.8, 27.0, 30.2, 30.4, 30.6, 30.8, 32.9 (CH$_2$), 38.5 (CH),
67.4 (C6),
72.6 (C5),
75.3 (OCH$_2$),
76.1 (C4),
76.3 (C2),
76.9 (C3),
102.6 (C1).

PHARMACOLOGICAL TEST EXAMPLE

Anti-inflammatory action to lung damage model induced by CVF Compounds obtained by Examples and an exemplary known compound (sulfatide) were selected as Test Compounds to check an inflammatory action thereof to a lung damage model induced by cobra venom factor (CVF), in accordance with the method described by M. S. Mulligan et al ["J. IMMUNOL.", Vol.151, page 6410 (1993); and "INT. IMMUNOL.", Vol. 7, page 1107 (1995)].

Namely, the test compound was intravenously injected by an amount of 0.2 mg/rat to test animals (Lewis rats, age of 8 weeks, 5 animals in each group). After lapsed 5 minutes from administration, CVF (20U/2 ml/kg) was administered in a tail vein, and after 30 minutes, a laparotomy was carried out under nembutal anesthesia to perfuse the lung with phosphate-buffered saline (PBS, pH7.4) by injecting the same from right ventricle and to exenterate the lung. The extracted lung was homogenized with phosphate buffer (pH 7.4), centrifuged to collect a supernatant, and determined absorbance which was admitted as index of bleeding (It measures an amount of hemoglobin and thus detection wave-length was set to 541 nm). Results are shown in following Table 1.

On the other hand, the precipitation obtained by centrifugation was sonicated in the presence of cetrimide and centrifuged to obtain a supernatant, an activity myeloperoxidase therein being measured as an index of infiltration in neutrocyte. Results are shown in following Table 2.

Each inhibition rate (%) was calculated by

100×[1−(value of test compound−value of negative control)/(value of positive control−value of negative control)].

Therefrom, it has been found that the compounds according to the invention show the anti-inflammatory action excellent than that of the sulfatide as exemplary known compounds.

TABLE 1

| Compound | Inhibition rate (%) |
|---|---|
| Example | |
| 1-1 | 22 |
| 1-2 | 16 |
| 2 | 36 |
| 3-1 | 27 |
| 3-2 | 49 |
| 4 | 39 |
| 5 | 52 |
| 6 | 0 |
| 7-1 | 36 |
| 7-2 | 42 |
| 8 | 53 |
| 9-1 | 84 |
| 9-2 | 100 |
| 10-1 | 65 |
| 10-2 | 63 |
| 11-1 | 100 |
| 11-2 | 82 |
| 12 | 0 |
| 13 | 43 |
| 14 | 55 |
| 15 | 45 |
| 16 | 75 |
| 17 | 74 |
| 18 | 50 |
| 19 | 43 |
| 20 | 45 |
| 21 | 64 |
| 22 | 65 |
| 23-1 | 53 |
| 23-2 | 51 |
| 24-1 | 54 |
| 24-2 | 50 |
| 25 | 56 |
| 26 | 56 |
| 27-1 | 65 |
| 27-2 | 62 |
| 28-1 | 63 |
| 28-2 | 63 |
| 29 | 67 |
| 30 | 70 |
| Sulfatide | 53 |

TABLE 2

| Compound | Inhibition rate (%) |
|---|---|
| Example | |
| 1-1 | 22 |
| 1-2 | 22 |
| 2 | 32 |
| 3-1 | 36 |
| 3-2 | 24 |
| 4 | 58 |
| 5 | 47 |
| 6 | 12 |
| 7-1 | 26 |
| 7-2 | 42 |
| 8 | 51 |
| 9-1 | 58 |

TABLE 2-continued

| Compound | Inhibition rate (%) |
|---|---|
| 9-2 | 86 |
| 10-1 | 66 |
| 10-2 | 82 |
| 11-1 | 82 |
| 11-2 | 70 |
| 12 | 30 |
| 13 | 46 |
| 14 | 41 |
| 15 | 44 |
| 16 | 70 |
| 17 | 73 |
| 18 | 51 |
| 19 | 39 |
| 20 | 40 |
| 21 | 52 |
| 22 | 58 |
| 23-1 | 51 |
| 23-2 | 49 |
| 24-1 | 47 |
| 24-2 | 49 |
| 25 | 50 |
| 26 | 50 |
| 27-1 | 61 |
| 27-2 | 58 |
| 28-1 | 60 |
| 28-2 | 55 |
| 29 | 65 |
| 30 | 62 |
| Sulfatide | 50 |

Medicine Preparation Example 1 (Tablet)

Tablets were prepared in a conventional manner and by using following ingredients.

| Compound (Example 16) | 2.0 (mg) |
|---|---|
| Lactose | 136.0 |
| Corn starch | 60.0 |
| Magnesium stearate | 2.0 |
| | 200.0 mg/tablet |

Medicine Preparation Example 2 (Injection)

A solution for injectional purpose was prepared in a conventional manner by using following ingredients and charged into ampules under aseptic condition to heat seal the ampules.

| Compound (Example 16) | 0.05 (mg) |
|---|---|
| Sodium chloride | 8.00 |
| Distilled water for injection | Remainder |
| | 1.0 ml/ampule |

What is claimed is:

1. A sulfated or phosphated saccharide derivative of the formula

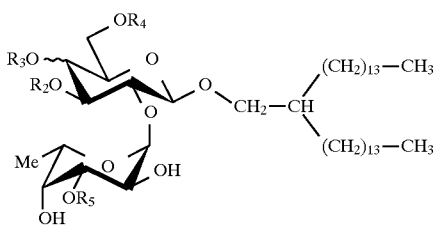

wherein $R_2$, $_4$ and $R_5$ are hydrogen atom or a residue of sulfate or phosphate, respectively with the proviso that at least one of $R_2$, $R_3$, $R_4$ and $R_5$ is sulfate or phosphate, or pharmaceutically acceptable salts thereof.

2. A sulfated or phosphated saccharaide derivative, or a salt thereof, selected from the group consisting of (i) 2-methylpropyl β-D-galactopyranoside 3-sulfate,
(ii) 2-methylpropyl β-D-galactopyranoside 6-sulfate,
(iii) 2-methylpropyl β-D-galactopyranoside 3,6-disulfate,
(iv) 2-methylpropyl β-D-galactopyranoside 3,4,6-trisulfate,
(v) 2-methylpropyl β-D-galactopyranoside 2,3,4,6-tetrasulfate,
(vi) 2-propylpentyl β-D-galactopylanoside 3-sulfate,
(vii) 2-propylpentyl β-D-galactopyanoside 6-sulfate,
(viii) 2-propylpentyl β-D-galactopyanoside 3,6-disulfate,
(ix) 2-propylpentyl β-D-galactopyanoside 2,3,6-trisulfate,
(x) 2-propylpentyl β-D-galactopyanoside 2,3,4,6-tetrasulfate,
(xi) 2-hexadecyltetracosyl β-D-galactopyranoside 3-sulfate,
(xii) 2-methylpropyl O-β-D-galactopyranosyl-(1→4)-β-D-glucopyranoside 3'-sulfate,
(xiii) 2-methylpropyl O-β-D-galactopyranosyl-(1→4)-β-D-glucopyranoside 3',6'-disulfate,
(xiv) 2-propylpentyl O-β-D-galactopyranosyl-(1→4)-β-D-glucopyranoside 3'-sulfate,
(xv) 2-propylpentyl O-β-D-galactopyranosyl-(1→4)-β-D-glucopyranoside 3',6'-disulfate,
(xvi) 2-tetradecylhexadecyl O-β-D-galactopyranosyl-(1→4)-β-D-glucopyranoside 3',6'-disulfate,
(xvii) 2-tetradecylhexadecyl O-β-D-galactopyranosyl-(1→4)-β-D-glucopyranoside 3',6',6-trisulfate,
(xviii) 2-methylpropyl β-D-galactopyranoside 2,3,4,6-tetraphosphate,
(xix) 2-propylpentyl β-D-galactopyranoside 2,3,4,6-tetraphosphate,
(xx) 2-tetradecylhexadecyl β-D-galactopyranoside 2,3,4,6-tetraphosphate,
(xxi) 2-methylpropyl β-D-galactopyranoside 3,4-diphosphate,
(xxii) 2-propylpentyl β-D-galactopyranoside 3,4-diphosphate,
(xxiii) 2-tetradecylhexadecyl β-D-galactopyranoside 3,4-diphosphate,
(xxiv) 2-propylpentyl β-D-glucopyranoside 3-phosphate,
(xxv) 2-propylpentyl β-D-galactopyranoside 2,3-diphosphate
(xxvi) 2-propylpentyl β-D-galactopyranoside 2,3,4-triphosphate
(xxvii) 2-propylpentyl O-β-D-galactopyranosyl-(1→4)-βD-glucopyranoside 3',4'-diphosphate,
(xxviii) 2-tetradecylhexadecyl O-β-D-galactopyranosyl-(1→4)-β-D-glucopyranoside 3',4'-diphosphate,
(xxix) 2-propylpentyl O-α-L-fucopyranosyl-(1→2)-β-D-galactopyranoside 3-sulfate,
(xxx) 2-propylpentyl O-α-L-fucopyranosyl-(1→2)-β-D-galactopyranoside 3,3'-disulfate,
(xxxi) 2-propylpentyl O-α-L-fucopyranosyl-(1→2)-β-D-galactopyranoside 3,6-disulfate,
(xxxii) 2-propylpentyl O-α-L-fucopyranosyl-(1→2)-β-D-galactopyranoside 3,3',6-trisulfate,
(xxxiii) 2-tetradecylhexadecyl O-α-L-fucopyranosyl-(1→2)-β-D-galactopyranoside 3-sulfate,
(xxxiv) 2-tetradecylhexadecyl O-α-L-fucopyranosyl-(1→2)-β-D-galactopyranoside 3,3'-disulfate,
(xxxv) 2-tetradecylhexadecyl O-α-L-fucopyranosyl-(1→2)-O-D-galactopyranoside 3,6-disulfate,
(xxxvi) 2-tetradecylhexadecyl O-α-L-fucopyranosyl-(1→2)-β-D-galactopyranoside 3,3',6-trisulfate,
(xxxvii) 2-propylpentyl O-α-L-fucopyranosyl-(1→2)-β-D-galactopyranoside 3-phosphate,
(xxxviii) 2-propylpentyl O-α-L-fucopyranosyl-(1→2)-βD-galactopyranoside 3,3'-diphosphate,
(xxxix) 2-tetradecylhexadecyl O-α-L-fucopyranosyl-(1→2)-β-D-galactopyranoside 3-phosphate,
(xxxx) 2-tetradecylhexadecyl O-α-L-fucopyranosyl-(1→2)-β-D-galactopyranoside 3,3'-diphosphate and
(xxxxi) a pharmaceutically acceptable salt of any of compounds (i)–(xxxx).

3. A process for the preparation of a sulfated or phosphated sacharide deriviative of the Formula

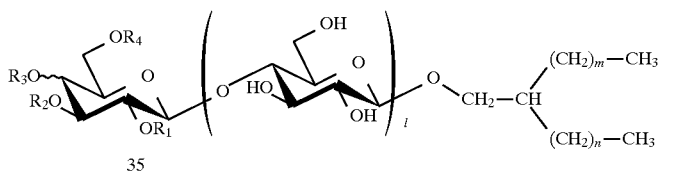

wherein $R_1$ is hydrogen atom or a residue of sulfate, phosphate or α-L-fucose; $R_2 R_3$ and $R_4$ are hydrogen atom or a residue of sulfate or phosphate, respectively; with the proviso that at least one of $R_1$, $R_2$, $R_3$ and $R_4$ is sulfate or phosphate and 1 is an integer of 0 or 1; m is an integer of 0–15; n is an integer of 0–21, or a pharmaceutically acceptable salt thereof, which comprises steps of reacting a compound of the Formula

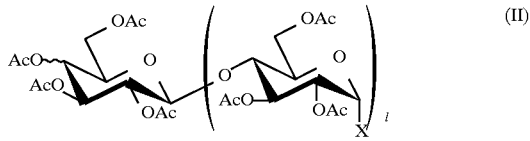

wherein X is a protecting group, with a compound of the Formula

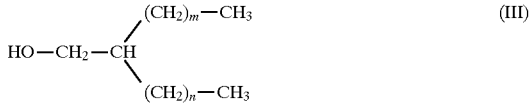

to produce a saccharide derivative shown by a Formula

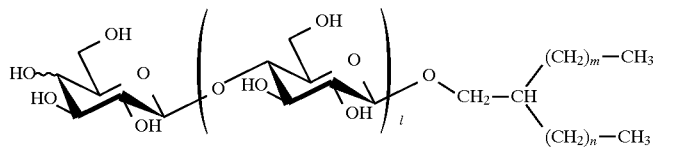

and then either:

reacting the saccharide derivative with di-n-butyl-tin oxide to make the saccharide derivative into its tin-acetal derivative, and then reacting the tin-acetal derivative with a complex of sulfite and trimethylammonium; or reacting the saccharide derivative with 2,2-dimethoxy propane and a benzyl halide to protect a group, removing the protecting group, and then reacting with dibenzyloxy (diisopropylamino) phosphine and 1H-tetrazole;

and if necessary, converting the resulting sulfated or phosphated saccharide derivative into the salt.

4. A pharmaceutical composition comprising at least one of sulfated or phosphated saccharide derivatives and pharmaceutical acceptable salts thereof, as claimed in claim 1, in an amount showing anti-inflammatory effect as well as a pharmaceutically acceptable carrier or excipient.

5. A pharmaceutical composition comprising at least one of sulfated or phosphated saccharide derivatives and pharmaceutical acceptable salts thereof, as claimed in claim 2, in an amount showing anti-inflammatory effect as well as a pharmaceutically acceptable carrier or excipient.

6. A process as recited in claim 3, further comprising converting said sulfated or phosphated saccharide derivative of Formula I into a salt.

\* \* \* \* \*